United States Patent [19]
Daniel et al.

[11] Patent Number: 5,860,992
[45] Date of Patent: Jan. 19, 1999

[54] ENDOSCOPIC SUTURING DEVICES AND METHODS

[75] Inventors: Sean Christopher Daniel, San Francisco; Brian S. Donlon, Los Altos Hills; Michi E. Garrison, Belmont; Hanson S. Gifford, III, Woodside; Daniel C. Rosenman, San Mateo, all of Calif.; William S. Peters, Elwood, Australia; Robert L. Lathrop, II, San Jose, Calif.; George Crothall, Santa Clara, Calif.; James B. Mullin, Pleasanton, Calif.; Gerald R. Anderson, Campbell, Calif.; Wiley A. Kittrell, Fremont, Calif.

[73] Assignee: Heartport, Inc., Redwood City, Calif.

[21] Appl. No.: 594,869

[22] Filed: Jan. 31, 1996

[51] Int. Cl.$^6$ .................................................. A61B 17/04
[52] U.S. Cl. ........................... 606/145; 606/139; 606/144
[58] Field of Search ................................... 606/144, 145, 606/148, 147, 139; 623/2

[56] References Cited

U.S. PATENT DOCUMENTS

| | | | |
|---|---|---|---|
| 1,449,087 | 3/1923 | Bugbee . | |
| 2,316,297 | 4/1943 | Southerland | 606/139 |
| 2,646,045 | 7/1953 | Priestley | 606/144 |
| 2,959,172 | 11/1960 | Held | 606/144 |
| 3,409,013 | 11/1968 | Berry | 128/303 |
| 3,946,740 | 3/1976 | Bassett . | |
| 4,027,608 | 6/1977 | Arbuckle | 112/169 |
| 4,042,979 | 8/1977 | Angell | 3/1.5 |
| 4,173,981 | 11/1979 | Mortensen | 128/348 |
| 4,217,665 | 8/1980 | Bex et al. | 3/1.5 |
| 4,235,177 | 11/1980 | Arbuckle | 112/169 |
| 4,406,237 | 9/1983 | Eguchi et al. | 112/169 |

(List continued on next page.)

FOREIGN PATENT DOCUMENTS

| | | |
|---|---|---|
| 0 218 275 | 4/1987 | European Pat. Off. . |
| 0 634 141 A1 | 1/1995 | European Pat. Off. ........ A61B 17/04 |
| 0 724 861A1 | 8/1996 | European Pat. Off. . |
| 18602 | of 1909 | United Kingdom . |
| 2260704 | 4/1993 | United Kingdom . |
| WO 93/20741 | 10/1993 | WIPO .............................. A61B 1/06 |
| WO 93/20742 | 10/1993 | WIPO .............................. A61B 1/06 |
| WO 95/06447 | 10/1993 | WIPO .............................. A61F 2/24 |
| WO 94/05213 | 3/1994 | WIPO ............................ A61B 17/00 |
| WO 94/15537 | 7/1994 | WIPO ............................ A61B 17/00 |

OTHER PUBLICATIONS

Berreklouw et al., "Revival of Right Thoractomy to Approach Atrio–ventricular Valves in Reoperations", 1984, *Thorac. Cardiovasc. Surgeon,* vol. 32, pp. 331–333.

G. D. Buckberg, "Strategies and Logic of Cardioplegic Delivery to Prevent, Avoid, and Reverse Ischemic and Reperfusion Damage", 1987, *J. Thorac. Cardiovasc. Surg.,* vol. 93, pp. 127–139.

Cohn et al., Right Thoracotomy, Femorofemoral Bypass, and Deep Hypothermia for Re–replacement of the Miral Valve, 1989, *Ann. Thorac. Surg.,* vol. 48, pp. 69–71.

Coltharp et al., "Videothorascopy: Improved Technique and Expanded Indications" 1992, *Ann. Thorac Surg.,* vol. 53, pp. 776–779.

(List continued on next page.)

*Primary Examiner*—Michael Buiz
*Assistant Examiner*—Tina T. D. Pham
*Attorney, Agent, or Firm*—Jeffry J. Grainger; Jens E. Hoekendijk

[57] ABSTRACT

The invention provides devices and methods for suture placement while performing less invasive surgical procedures within a body cavity. In an exemplary embodiment, the invention provides for the placement of sutures within the heart or a great vessel that is accessed from outside the closed chest. According to one exemplary method, the patient's heart valve is accessed through an intercostal port in the patient's chest. At least one needle having a suture is then directed into the annulus while visualizing through the port placement of the needle into the annulus. The needle is then passed through the annulus.

23 Claims, 24 Drawing Sheets

U.S. PATENT DOCUMENTS

| | | | |
|---|---|---|---|
| 4,414,908 | 11/1983 | Eguchi et al. | 112/169 |
| 4,417,532 | 11/1983 | Yasukata | 112/169 |
| 4,437,465 | 3/1984 | Nomoto et al. | 128/340 |
| 4,440,171 | 4/1984 | Nomoto et al. | 128/335.5 |
| 4,465,070 | 8/1984 | Eguchi | 128/334 R |
| 4,484,580 | 11/1984 | Nomoto et al. | 128/340 |
| 4,489,446 | 12/1984 | Reed | 3/1.5 |
| 4,553,544 | 11/1985 | Nomoto et al. | 128/340 |
| 4,557,265 | 12/1985 | Andersson | 128/340 |
| 4,621,640 | 11/1986 | Mulhollan et al. . | |
| 4,655,218 | 4/1987 | Kulik et al. | 128/321 |
| 4,702,250 | 10/1987 | Ovil et al. | 128/334 |
| 4,747,358 | 5/1988 | Moll et al. | 112/169 |
| 4,898,155 | 2/1990 | Ovil et al. . | |
| 4,899,746 | 2/1990 | Brunk | 606/144 |
| 4,917,698 | 4/1990 | Carpentier et al. | 623/2 |
| 4,932,965 | 6/1990 | Phillips | 623/2 |
| 5,011,481 | 4/1991 | Myers et al. | 606/1 |
| 5,032,128 | 7/1991 | Alonso | 623/2 |
| 5,041,130 | 8/1991 | Cosgrove et al. | 623/2 |
| 5,061,277 | 10/1991 | Carpentier et al. | 623/2 |
| 5,064,431 | 11/1991 | Gilbertson et al. | 623/2 |
| 5,080,663 | 1/1992 | Mills et al. . | |
| 5,084,058 | 1/1992 | Li . | |
| 5,087,263 | 2/1992 | Li . | |
| 5,100,415 | 3/1992 | Hayhurst . | |
| 5,104,407 | 4/1992 | Lam et al. | 623/2 |
| 5,109,859 | 5/1992 | Jenkins | 128/662.03 |
| 5,152,769 | 10/1992 | Baber | 606/145 |
| 5,163,946 | 11/1992 | Li . | |
| 5,188,619 | 2/1993 | Myers | 604/280 |
| 5,196,022 | 3/1993 | Bilweis . | |
| 5,196,023 | 3/1993 | Martin . | |
| 5,197,979 | 3/1993 | Quintero et al. | 623/2 |
| 5,201,880 | 4/1993 | Wright et al. | 623/2 |
| 5,203,776 | 4/1993 | Durfee | 604/264 |
| 5,211,650 | 5/1993 | Noda . | |
| 5,222,962 | 6/1993 | Burkhart . | |
| 5,224,948 | 7/1993 | Abe et al. | 606/147 |
| 5,250,038 | 10/1993 | Melker et al. | 604/264 |
| 5,257,999 | 11/1993 | Slanetz, Jr. . | |
| 5,258,021 | 11/1993 | Duran | 623/2 |
| 5,290,300 | 3/1994 | Cosgrove et al. | 623/2 |
| 5,306,296 | 4/1994 | Wright et al. | 23/2 |
| 5,308,320 | 5/1994 | Safar et al. | 604/4 |
| 5,308,353 | 5/1994 | Beurrier | 606/144 |
| 5,332,402 | 7/1994 | Teitelbaum | 623/2 |
| 5,350,420 | 9/1994 | Cosgrove et al. | 623/2 |
| 5,374,275 | 12/1994 | Bradley et al. | 606/144 |
| 5,376,112 | 12/1994 | Duran | 623/2 |
| 5,387,221 | 2/1995 | Bisgaard | 606/148 |
| 5,387,227 | 2/1995 | Grice | 606/222 |
| 5,389,103 | 2/1995 | Melzer et al. | 606/144 |
| 5,391,156 | 2/1995 | Hildwein et al. | 604/174 |
| 5,391,174 | 2/1995 | Weston . | |
| 5,397,325 | 3/1995 | Della Badia et al. . | |
| 5,403,305 | 4/1995 | Sauter et al. | 606/1 |
| 5,403,328 | 4/1995 | Shallman | 606/144 |
| 5,403,329 | 4/1995 | Hinchcliffe | 606/147 |
| 5,437,681 | 8/1995 | Meade et al. . | |
| 5,454,823 | 10/1995 | Richardson et al. | 606/148 |
| 5,470,338 | 11/1995 | Whitfield et al. | 606/144 |
| 5,474,568 | 12/1995 | Scott | 606/144 |
| 5,540,375 | 7/1996 | Bolanos et al. . | |
| 5,540,705 | 7/1996 | Meade et al. . | |
| 5,571,119 | 11/1996 | Atala | 606/146 |
| 5,575,800 | 11/1996 | Gordon | 606/144 |
| 5,613,937 | 3/1997 | Garrison et al. | 606/201 |
| 5,630,825 | 5/1997 | de la Torre et al. . | |

OTHER PUBLICATIONS

D. M. Cosgrove, "Management of the Calcified Aorta: An Alternative Method of Occlusion", 1983, *Ann. Thorac. Surg.*, vol. 36, pp. 718–719.

H. G. Erath, Jr. and W.S. Stoney, Jr., "Balloon Catheter Occlusion of the Ascending Aorta", 1983, *Ann. Thorac. Surg.*, vol. 35, pp. 560–561.

Foster et al., "Proximal Control of Aorta with a Balloon Catheter", 1971, *Surg. Gynecology & Obstetrics*, pp. 693–694.

Fundaro et al., "Towards an Easier and Safer Reoperation of the Atrioventricular Valves the Right Anterolateral Thoracotomy Approach without Pericardial Dissection", 1989, *J. Cardiovasc. Surg.*, vol. 30, pp. 779–781.

W. R. Eric Jamieson, "Modern Cardiac Valve Devices–Bioprostheses and Mechanical Prostheses: State of the Art", 1 993, *J.Card. Surg.*, vol. 8, pp. 89–98.

Landreneau et al., "Video–Assisted Thoracic Surgery: Basic Technical Concepts and Intercostal Approach Strategies" *Ann. Thorac Surg.*, 1992, vol. 54, pp. 800–807.

Laurus Medical Corp., "The Laurus In–Line Endoscopic Suturing Device", 1994, *Product Brochure*, Rev. 10.

Mack et al., "Present Role of Thoracoscopy in the Diagnosis and Treatment of Diseases of the Chest", 1992, *Ann. Thorac Surg.*, vol. 54, pp. 403–409.

G. J. Magovern, "Sutureless Aortic and Mitral Prosthetic Valves", 1964, *J. Thoracic and Cardiovasc. Surg.*, vol. 48, pp. 346–361.

Medi•tech®, Instructions for Use, Occlusion Balloon Catheters, Rev. Mar. 1991, pp. 1–7.

Melzer et al., "Future Trends in Endoscopic Suturing", 1994, *End. Surg.*, vol. 2, pp. 78–82.

Ozuner et al., "Creation of a Pericardial Window Using Thoracoscopic Techniques", 1992, *Surg. Gynecology & Obstetrics*, vol. 175, pp. 69–71.

W. S. Peters, "Minimally Invasive Cardiac Surgery by Cardioscopy", 1993, *Australia J. Cardiac. Thorac. Surg.*, vol. 2, No. 3, pp. 152–154.

REMA–Medizintechnik GmbH, "Innovation Through Progress", *Product Brochure*.

Sakaguchi et al., "Aortic Valve Replacement and Coronary Artery Bypass", 1993, *J. Japanese Assoc. for Thoracic Surgery*, vol. 41, No. 6, pp. 1063–1068.

Tribble et al., "Anterolateral Thoracotomy as an Alternative to Repeat Median Sternotomy for Replacement of the Mitral Valve", 1987, *Ann. Thorac. Surg.*, vol. 43, pp. 380–382.

Wakabayashi, Akio, "Expanded Applications of Diagnostic and Therapeutic Thoracoscopy", 1991, *J. Thorac and Cardiovasc. Surg.*, vol. 102, pp. 721–723.

Yamaguchi et al., "A Case of a Reoperation Using a Balloon Catheter With Blocked Pars Acendes Aortae", 1991, *Kyobu Geka*, vol. 42, No. 11, pp. 961–964.

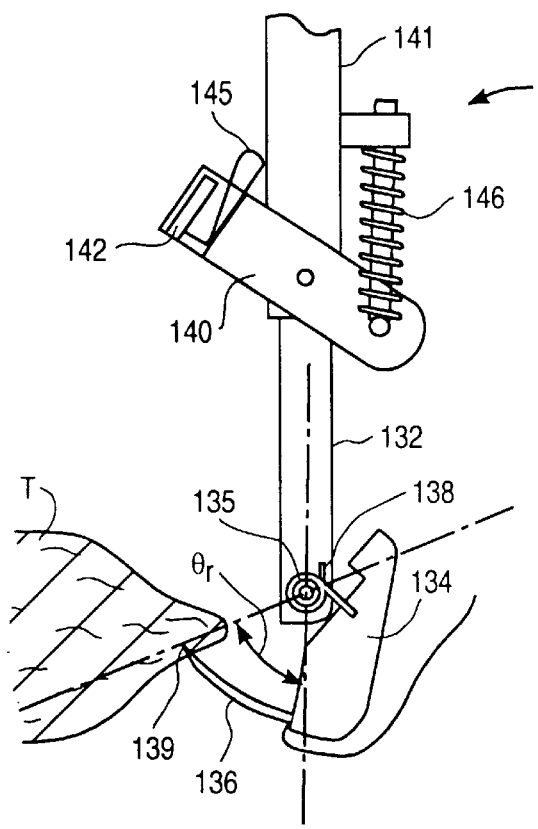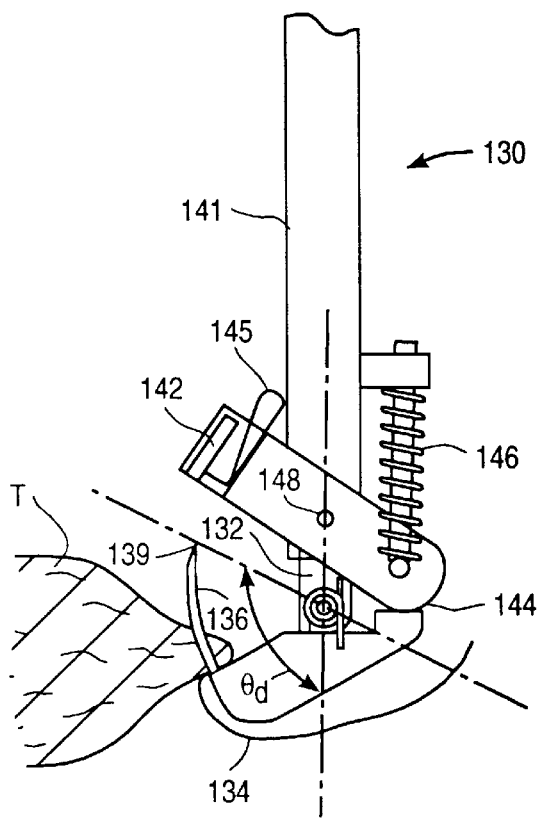
FIG. 19  FIG. 20
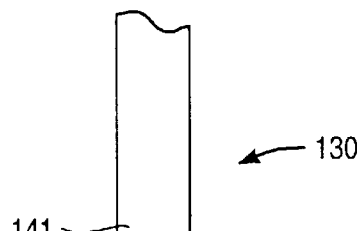
FIG. 21
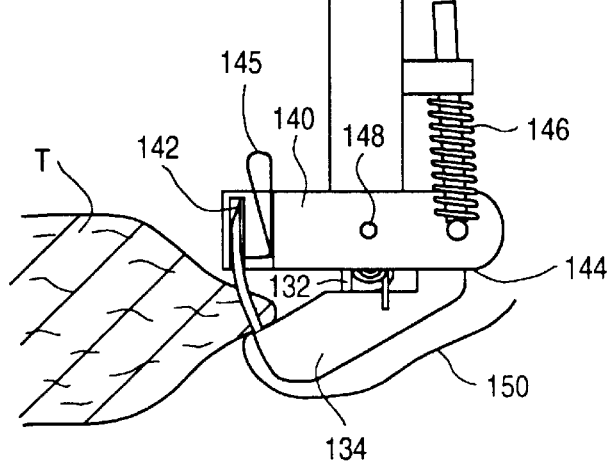

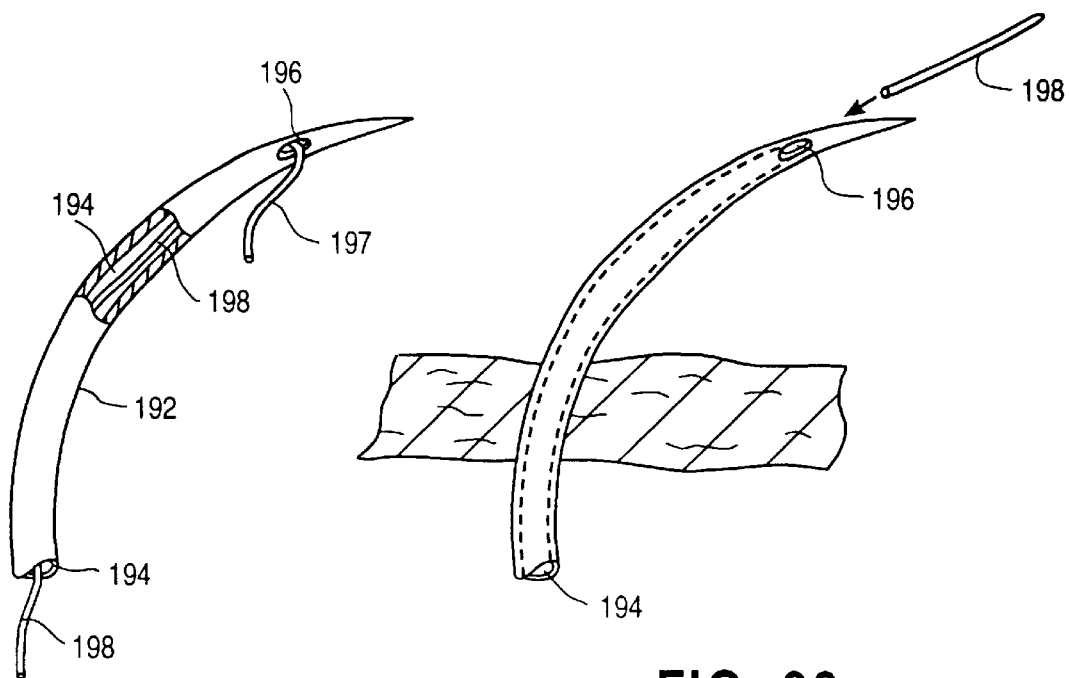
FIG. 27
FIG. 28
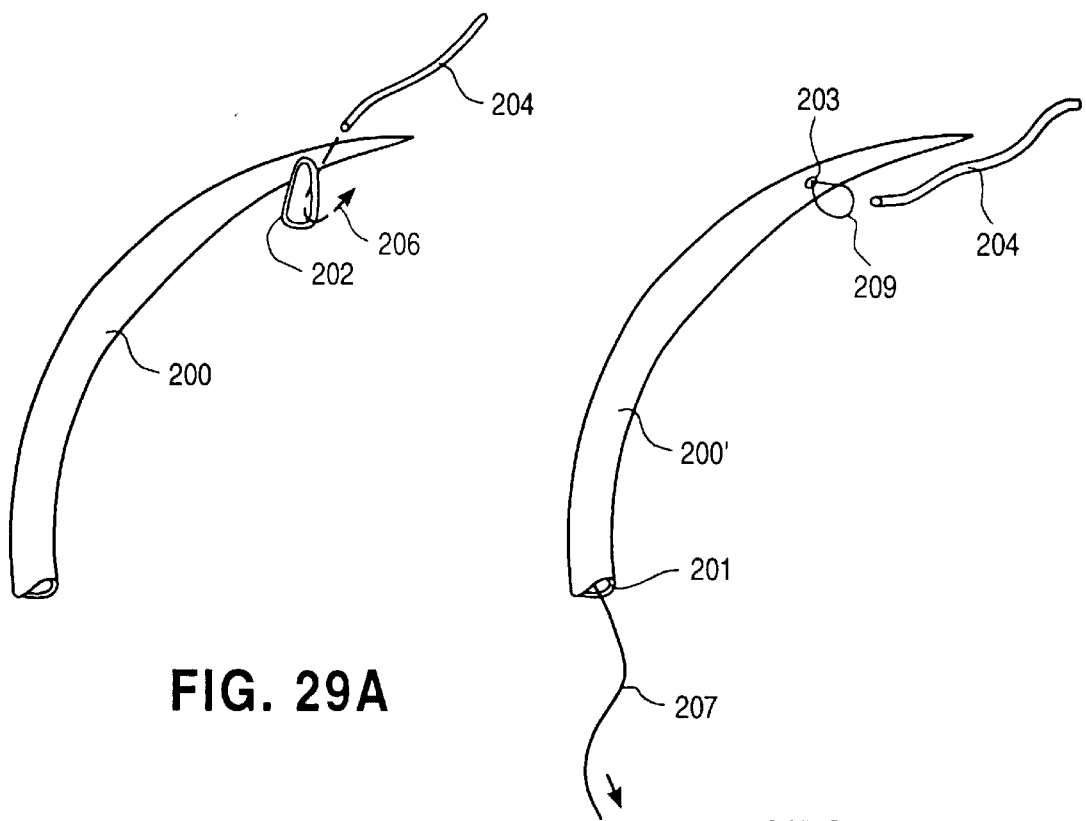
FIG. 29A
FIG. 29B

ENDOSCOPIC SUTURING DEVICES AND METHODS

BACKGROUND OF THE INVENTION

1. Field of the Invention

This invention relates generally to the field of surgical procedures, and in particular to the placement of a suture in tissue. More specifically, the invention relates to suture placement devices and techniques for less invasive surgical procedures within the heart and great vessels.

Various types of surgical procedures are currently performed to investigate, diagnose, and treat diseases of the heart and the great vessels of the thorax. Such procedures include repair and replacement of mitral, aortic, and other heart valves, repair of atrial and ventricular septal defects, pulmonary thrombectomy, treatment of aneurysms, electrophysiological mapping and ablation of the myocardium, and other procedures in which interventional devices are introduced into the interior of the heart or a great vessel.

Of particular interest to the present invention are intracardiac procedures for surgical treatment of heart valves, especially the mitral and aortic valves. According to recent estimates, more than 79,000 patients are diagnosed with aortic and mitral valve disease in U.S. hospitals each year. More than 65,000 mitral valve and aortic valve replacement procedures are performed annually in the U.S., along with a significant number of heart valve repair procedures.

Various surgical techniques may be used to repair a diseased or damaged vessel, including annuloplasty (contracting the valve annulus), quadrangular resection (narrowing the valve leaflets), commissurotomy (cutting the valve commissures to separate the valve leaflets), shortening mitral and tricuspid valve chordae tendonae, reattachment of severed mitral or tricuspid valve chordae tendonae or papillary muscle tissue, and decalcification of valve and annulus tissue. Alternatively, the valve may be replaced, by excising the valve leaflets of the native valve, and securing a replacement valve in the valve position, usually by suturing the replacement valve to the natural valve annulus. Various types of replacement valves are in current use, including mechanical and biological prostheses, homografts, and allografts, as described in Bodnar and Frater, *Replacement Cardiac Valves*, 1–357 (1991). A comprehensive discussion of heart valve diseases and the surgical treatment thereof is found in Kirklin and Sir Brian Barratt-Boves, *Cardiac Surgery*, 323–459 (1986).

When investigating, diagnosing, or treating diseases of the heart and the great vessels of the thorax, many current techniques require a gross thoracotomy, usually in the form of a median sternotomy, to gain access into the patient's thoracic cavity. A saw or other cutting instrument is used to cut the sternum longitudinally, allowing two opposing halves of the anterior or ventral portion of the rib cage to be spread apart. A large opening into the thoracic cavity is thus created, through which the surgical team may directly visualize and operate upon the heart and other thoracic contents.

Less-invasive surgical procedures have recently been developed which avoid the need for a gross thoracotomy, such as a median sternotomy. In such less invasive procedures, access to the thoracic cavity is obtained through percutaneous penetrations within intercostal spaces of the rib cage. Through such intercostal penetrations, surgical instruments may be inserted to therapeutically treat the heart or thoracic contents. For example, U.S. Pat. No. 5,571,215, the disclosure of, which is hereby incorporated by reference, describes techniques for less-invasive heart valve replacement wherein a diseased heart valve may be replaced with a prosthetic valve utilizing small-profile instruments introduced through percutaneous access ports, incisions or punctures between the ribs. Similarly, application Ser. No. 08/485,600, filed Jun. 7, 1995, which is incorporated herein by reference, discloses techniques for repair of cardiac valves by securing an annuloplasty ring to the valve annulus using instruments positioned through small, percutaneous access ports between the ribs.

Common to many cardiac surgical procedures is the need to place sutures in heart or other tissue within the thoracic cavity. For example, in the case of heart valve repair or replacement, the valve prosthesis or annuloplasty ring is usually sutured to tissue on or around the patient's native valve annulus.

Placing sutures in heart or other tissue that is accessed from outside of the patient's chest through small access ports presents a variety of difficulties. For instance, maneuverability is often difficult due to the limited space between the ribs. Further, when accessing the contents of the thoracic cavity through an intercostal space, visibility is limited, thereby making it difficult to properly place the suture. Further, such procedures can become timeconsuming, particularly when placing a single suture at a time. Placing sutures in an annulus of a heart valve for attachment of a replacement valve or annuloplasty ring is especially challenging. The suture needle must be inserted through the valve annulus in a direction toward or away from the surgeon, creating difficulty in seeing and manipulating the needle as it is passes through the annulus. Frequently, a curved needle is used in order to drive the needle deeper into the annulus tissue so that the suture will not tear out of the tissue. However, such a curved needle must be driven in an arc about an axis parallel to the plane of the annulus, whereas in less-invasive procedures, the surgical approaches used to access the heart valves dictate that the needleholding instrument be oriented at an angle perpendicular to the plane of the annulus. The needle must therefore be driven in a curved path about an axis roughly perpendicular to the shaft of the instrument. With the angular motion of the instrument highly limited when positioned through a small intercostal access port, the ability to drive a curved needle in an arcuate path through the valve annulus is greatly compromised.

What is needed, therefore, are devices and methods for improved suture placement when access to the tissue is limited, such as in less-invasive surgical procedures. In particular, the devices and methods should allow for improved visibility of the needle as it is either placed into or removed from tissue. Preferably, the devices and methods will provide the ability to conveniently introduce the needle tip into tissue, remove it, and then replace it in a separate location in the event that the needle was initially misplaced. The devices and methods should also facilitate easy introduction and passage of the needle through tissue. The devices and methods should also reduce the time required to place the sutures. In a preferable aspect, the devices and methods should facilitate the placement of sutures in a native valve annulus in the heart for attachment of various types of protheses, including mechanical and biological prostheses, homografts, allografts, annuloplasty rings, and the like. The devices and methods should further facilitate driving a curved suture needle in an arcuate path through the native valve annulus using an instrument oriented perpendicular to the plane of the annulus. The devices and methods should be useful not only in conventional open surgical procedures, but should be suitable for use through small percutaneous access ports in less-invasive surgical procedures as well.

2. Brief Description of the Background Art

A variety of suturing instruments are described in U.S. Pat. Nos. 4,027,608; 4,235,177; 4,406,237; 4,414,908; 4,417,532; 4,440,171; 4,465,070; 4,474,358; 4,484,580; 4,553,544; 4,557,265; 4,899,746; 5,152,769; 5,224,948; 5,308,353; 5,374,275; 5,403,328; 5,403,329; 5,403,329; 5,403,328; 5,224,948; and PCT Applications WO 94/05213, WO 94/15537 and WO 95/06447.

Product brochure, *The Laurus In-line Endoscopic Suturing Device*, Laurus Medical Corporation, Irvine, Calif., rev. 10/94, describes an "in-line needle driver" which includes an elongate shaft with an interior channel at a distal end of the shaft. The interior channel allows a needle to be loaded into the shaft so that needle is generally completely housed within the shaft when fully loaded.

Product brochure, *Innovation Through Progress*, Rema-Medizintechnik GmbH, describes a suturing device for closing wounds during laparoscopic operations. The device includes an elongate shaft having a pair of lateral needles which are generally parallel to the shaft. The needles may be extended away from the shaft after insertion of the device through endoscopic working channels so that the needles may be pulled through the tissue.

U.S. Pat. No. 4,932,965 describes an artificial valve having a holder for holding sutures and needles used when implanting the valve.

SUMMARY OF THE INVENTION

The invention provides devices and methods for placement of sutures in tissue structures, particularly tissue structures which cannot be easily accessed or visualized using conventional instruments. The devices and methods of the invention are especially useful in less invasive surgical procedures within an organ or vessel, and particularly, within the heart and great vessels of the thoracic cavity. In an exemplary embodiment, the invention provides devices and methods for placing sutures in tissue located within the thoracic cavity, where access to the thoracic cavity is obtained through percutaneous penetrations within intercostal spaces of the patient's rib cage, without cutting, removing, or significantly displacing any of the patient's ribs or sternum. The devices and methods are particularly well adapted in procedures for heart valve repair and replacement. The devices and methods are especially useful for placement of sutures in annular structures such as a heart valve annulus. For instance, the devices and method may be used to attach mechanical valve prostheses, bioprostheses, homografts, allografts, annuloplasty rings, and the like to a native valve annulus of the heart.

In a particularly preferable embodiment, a method is provided for placing a suture in the annulus of a heart valve that is accessed through an intercostal port in the patient's chest. According to the method, a needle which is attached to the suture is positioned in the patient's heart. The needle is removably coupled to a distal end of an elongated shaft extending through the port. The needle is directed into the annulus while visualizing through the port placement of the needle into the annulus. Following placement of the needle into the annulus, the needle is further directed through the annulus by manipulating an actuator at a proximal end of the shaft from outside of the patient's chest. In one preferable aspect, a step is provided for directly looking through the port to visualize placement of the needle while the shaft extends through the port.

Usually, the sharp tip of the needle will be proximally advanced from a far side of the annulus facing away from the surgeon so that it will exit a near side of the annulus facing the surgeon. In this way, the surgeon may directly visualize the sharp tip of the needle through the port as it exits the annulus. In the event that the sharp tip exits at an undesirable location in the annulus, the sharp tip may be retracted from the annulus and redirected into the annulus at a different location. In an alternative step, the needle may be advanced into the annulus from the near side until it exits the far side of the annulus. Optionally, visualization of needle placement may be accomplished through a port in the patient's chest other than that through which the elongate shaft is introduced. If desired, a visualization device, such as an endoscope, laparoscope, or thoracoscope, may be employed to assist in visualizing needle placement.

In one particular aspect, the needle has a curvature and is directed through the tissue in an arc generally conforming to the curvature of the needle. In this way, passage of the curved needle through the tissue is facilitated with minimal friction. Further, the curved geometry of the needle assists in ensuring that the needle will sufficiently "bite" into the annulus so that the suture may be placed a sufficient distance into the tissue from the edge of the annulus. Rotation of the needle in such an arc is further advantageous in reducing the force required to drive the needle through the tissue since the needle passes through the tissue about its own arc. In this way, substantially the entire needle (except that portion actually within the tissue) may be viewed while the needle is being driven through tissue.

In another particular aspect, the elongate shaft has an axis between the proximal and distal ends. The needle is driven within a plane parallel to the axis of the shaft, or within about 45° of the plane, and preferably within about 20° of the plane. Usually, the sharp tip of the needle will be driven through an arc of at least about 90° relative to the axis of the shaft, preferably from about 90° to 270°, and more preferably from about 90° to 180°. In most cases, the sharp tip of the needle will usually be at a starting position at about 0° to 90°, and preferably 45° to 80° relative to the shaft axis and will be moved to an ending position at about 90° to 180° relative to the shaft axis. In this way, the needle may be driven with minimal or no lateral movement of the shaft.

In another aspect, the sharp tip of the needle is rotated in an arc first away from the shaft, then back toward the shaft as it is rotated through the arc. In yet another aspect, the needle is passed sufficiently through the annulus so the distal end may be grasped and pulled through the tissue, with the proximal end of the needle becoming detached from the shaft. Detachment of the proximal end of the needle may occur by grasping the sharp tip with a separate instrument and pulling the needle from the shaft. Alternatively, the shaft may include a needle catch for receiving the sharp tip and pulling the proximal end of the needle away from the shaft.

In still another aspect, the needle is removably attached to a needle holder, which in turn is removably attached to the shaft. In this manner, the needle holder may be removed from the shaft and replaced with a different needle holder. Such a configuration is advantageous in allowing for different sizes, shapes, and styles of needles to be attached to the same shaft by merely providing needle holders that are adapted to hold various types of needles. The removable needle holder is also advantageous in that it may be made of a disposable material and thrown away after each use, allowing the shaft to be sterilized and reused after a surgical procedure.

In still a further aspect, a plurality of (usually two) needles are simultaneously directed into the annulus. Two or more needles may be held in a single needle holder side-by-side, or each needle may be held in its own needle holder attached to the end of the shaft.

In another aspect, the annulus is supported during the directing step. The annulus may be supported by clamping the annulus between two surfaces of a clamping mechanism attached to the shaft. One of the surfaces is usually translated relative to the other surface so as to compress the annulus tissue therebetween. Alternatively, the annulus may be supported by positioning a supporting surface behind the annulus to oppose the force of the needle as it is advanced through the annulus.

In another embodiment, the invention provides an exemplary method for placing a suture in tissue adjacent to an opening in a body structure. The method comprises providing at least one needle having a curvature and a sharpened tip. The needle is coupled to a distal end of an elongate shaft. The sharpened tip is directed into the tissue adjacent the opening, and the needle is passed through the tissue in an arc generally conforming to the needle curvature by manipulating an actuator at a proximal end of the shaft. The sharpened tip may be either proximally advanced (from a far side to a near side) or distally advanced (from a near side to a far side) through the tissue.

In a preferable aspect, the sharpened tip is directed into the annulus of a heart valve. In one exemplary aspect, the valve is the mitral valve, and the passing step further comprises passing the needle from the atrium to the ventricle. Alternatively, the needle may be passed from the ventricle to the atrium. In another aspect, the valve is the aortic valve, and the passing step comprises passing the needle either from the ventricle to the aorta or from the aorta to the ventricle. In still a further aspect, a prosthetic device such as an annuloplasty ring or a heart valve is secured to the heart tissue with the suture.

In an additional embodiment, a suture device according to the invention comprises an elongate needle driver body having a proximal end and a distal end. A needle holder is operably attached to the distal end of the needle driver body and a driving mechanism is coupled to the needle holder at the distal end for moving the needle holder. At least one needle is releasably held by the needle holder, with the needle having a length of suture attached thereto. A suture tensioner is attached to the needle driver body proximal to the needle, with the suture tensioner including a suture holding mechanism for holding the length of suture in tension. In this way, the suture tensioner may be employed to maintain the free length of suture in tension, such as when introducing the suture device to a target location. The suture tensioner may be either fixedly or slidable mounted to the driver body. In one exemplary aspect, the needle holder is movably attached to the distal end of the driver body.

The invention further provides a suturing device comprising, in an exemplary embodiment, an elongate shaft with a distal end and a proximal end. At least one needle is operably attached near the distal end of the shaft. A tissue holder is provided near the distal end of the shaft for supporting a layer of tissue. A needle driving mechanism is mounted to the shaft spaced apart from the tissue holder for driving the needle through the tissue secured by the tissue holder.

In an exemplary aspect, the tissue holder comprises a pair of spaced-apart surfaces for clamping the layer of tissue. In one aspect, one of the surfaces is pivotable or slidable relative to the other surface. In an alternative aspect, the tissue holder comprises a single surface that is spaced apart from the needle. As the needle is advanced into the tissue, the surface prevents movement of the tissue so that the needle may be driven therethrough.

In another exemplary aspect, the needle driver comprises a needle carriage for removably holding the needle. The carriage is preferably pivotally attached to the shaft so that the needle may be rotated within a plane parallel to the axis of the shaft or within about 45° of the plane, and preferably within about 20° of the plane. Preferably, the carriage will be attached to pivot through an angle of at least 90° relative to the axis of the shaft, preferably from about 90° to 270°, and more preferably from about 90° to 180°. In most cases, the tip of the needle will usually be at a starting position at about 0° to 90°, preferably 45° to 80°, relative to the shaft axis and will be rotated to an ending position at about 90° to 180°, preferably 135° to 170° relative to the shaft axis.

In still a further aspect, the needle driver comprises a rod that is slidably coupled to the shaft and attached to the carriage to pivot the carriage relative to the shaft. Optionally, at least a portion of the shaft may be curved to facilitate viewing and manipulation of the needle when viewing the needle from the proximal end of the shaft. In such a case, the rod may be constructed of a super elastic material, such as Nitinol™ (Raychem Corp.).

In one preferable aspect, a needle catch is provided which captures and removes the needle from the needle driving mechanism. In one aspect, the needle catch comprises a slot in the driving mechanism or in the shaft. Alternatively, the needle catch comprises a grasping instrument fixed or slidable along the shaft and having a pair of movable jaws for grasping the needles to remove it from the driving mechanism.

In another particular aspect, the needle is curved in geometry. The needle is preferably provided with a radius that is substantially equal to the radial distance of the needle from its pivotal attachment to the carriage—that is, the needle is mounted such that its center of curvature and center of rotation are at the same position. In this way, the needle may be moved in an arc substantially conforming to the curvature of the needle. In an alternative aspect, the needle is straight in geometry. In still a further aspect, the needle carriage is removably attached to the shaft so that the shaft can be reused with different needle carriages, particularly with those having different sized needles. The carriage may be made of a biocompatible plastic so that it may be disposed of after a single use, while the remainder of the device is sterilized and re-used. Alternatively, the entire suture device may be constructed to be disposable, such as, for example, constructing the handle of a plastic material. In this manner, the entire suture device may be disposed after a procedure.

In still a further aspect, the suturing device is provided with a handle assembly at the proximal end of the shaft. The handle assembly includes an actuator for translating the rod which in turn pivots the carriage. The actuator may comprise a slidable button, pivotable lever, trigger, or other mechanism. Optionally, the handle assembly may be provided with a button lock for preventing movement of the actuator at a selected position.

The shaft preferably has a length of at least 20 cm so that the suture may be placed in tissue located within the thoracic cavity while the handle is grasped and operated from outside the patient's chest. The suturing device is preferably configured to pass easily through a tubular space (such as a thoracic port or trocar sleeve) having an inner diameter of less than 30 mm, usually less than 20 mm, and preferably less than 12 mm, depending upon the size and shape of the needle used. The profile of the device is minimized so that sufficient space is provided between the intercostal port and the shaft so that placement of the needle may be directly visualized through the port. In still a further aspect, the handle assembly and shaft are preferably constructed of an autoclavable material such as stainless steel.

In an alternative aspect, the needle is configured to be inserted through a layer of tissue so that its tip is exposed, then a length of suture material is attached to the exposed tip, and the needle retracted with the suture back through the tissue. In one embodiment, the needle has a longitudinal passage through it with openings near the proximal and distal ends of the needle. In this way, when the tip of the needle is passed through the tissue, the suture may be inserted into the distal opening into the longitudinal passage and threaded through the needle and out of the proximal opening in the longitudinal passage. A vacuum may be applied to the proximal opening to assist in this process. Alternatively, a means for attaching the suture may be provided at the distal end of the needle, such as a slot or hole in the needle or a flexible loop attached to the needle. Alternatively, the loop may be a wire which extends out of the distal opening so that the suture may be grasped when pulling the wire to close the loop.

Hence, the present invention provides methods and apparatus which facilitate suture placement in tissue which cannot easily be accessed or visualized. For example, by manipulating an actuator at a proximal end of a shaft to rotate a curved needle about its curvature, the needle tip may be placed into and passed through tissue which is difficult to reach. Such a construction also allows for direct visualization of substantially the entire needle throughout the suturing process, particularly with less invasive procedures where direct visualization is often limited to a line of sight through an access port or trocar.

BRIEF DESCRIPTION OF THE DRAWINGS

FIG. 5A is a perspective view of an exemplary insert included in the removable portion of FIG. 5 for holding a needle.

FIGS. 19–21 illustrate still yet another alternative embodiment of a suturing device having a slightly curved needle that is held in a swinging needle holder and a swinging needle catch according to the present invention.

FIG. 27 illustrates an exemplary hollow needle having a length of suture extending therethrough according to the present invention.

FIG. 28 illustrates the hollow needle of FIG. 28 receiving a length of suture through an aperture at its distal end.

FIG. 29A illustrates an alternative embodiment of a needle having a loop for attaching a length of suture according to the present invention.

FIG. 29B illustrates another alternative embodiment of a needle having a lasso for capturing and securing a length of suture according to the present invention.

DETAILED DESCRIPTION OF THE SPECIFIC EMBODIMENTS

The invention provides methods and devices for the placement of sutures in tissue. The devices and methods may be used in a wide variety of surgical procedures where suture placement is required and will find particular use in lessinvasive surgical procedures within the abdomen, pelvis, and thorax. The methods and apparatus will be particularly useful in facilitating suture placement about a rim, lip, or annulus of tissue, or through an incision, that is located anywhere in the body. The methods and apparatus are particularly useful when visual access to such tissue is limited. In many cases, the tissue receiving the suture will be accessed through percutaneous penetrations within intercostal spaces of the rib cage or in the abdomen or pelvis, obviating the need for a large open incision.

While the specific embodiments of the invention described herein will refer to suture placement in procedures involving repair or replacement of a specific heart valve, it should be understood that the invention will be useful in a variety of surgical procedures, including repair or replacement of mitral, aortic, tricuspid, or pulmonary valves, repair of atrial and ventricular septal defects, hernia repairs, fascia closure, and other procedures requiring placement of sutures in body tissues. The devices and methods will find particular use in attaching a wide variety of prosthetic devices, including mechanical and biological prostheses, homografts, allografts, annuloplasty rings, and the like during such procedures. Most preferably, the devices and methods will be useful when placing a suture in tissue where access and visualization are limited, such as about the periphery of an opening in tissue (e.g. such as in the annulus of a heart valve or in tissue surrounding an incision).

Figure 1:
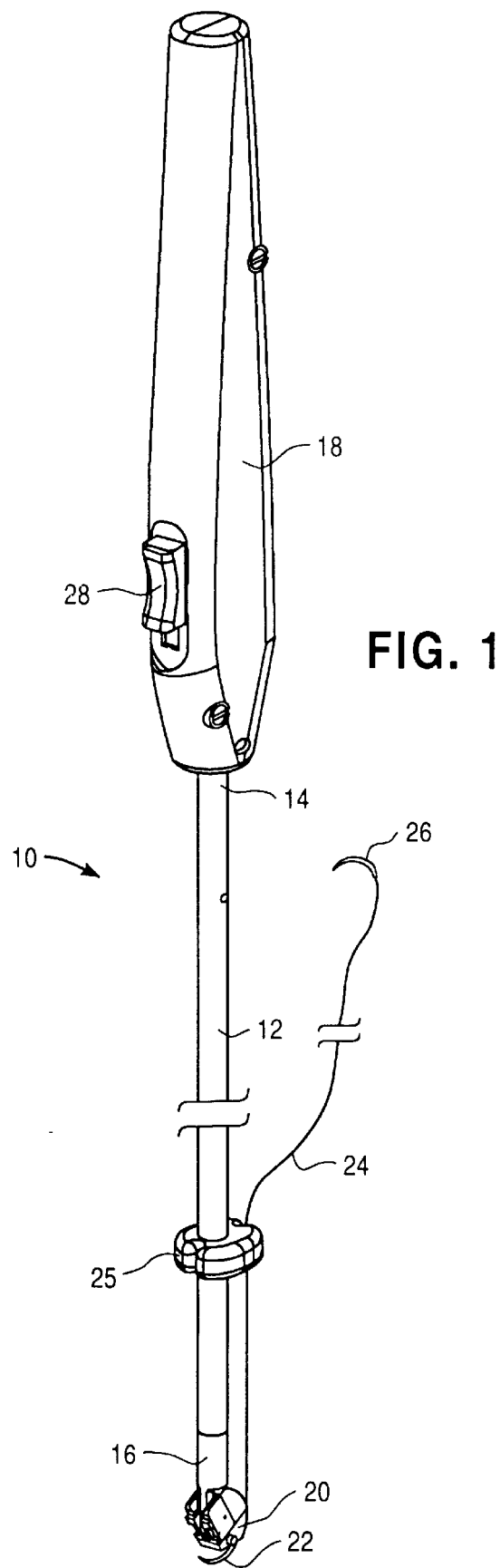
FIG. 1 is a perspective view of an exemplary embodiment of a suturing device according to the present invention.
Figure 1A:
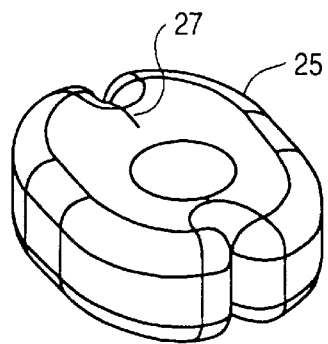
FIG. 1A is a perspective view of a suture holder of the suturing device of FIG. 1.
Figure 2:
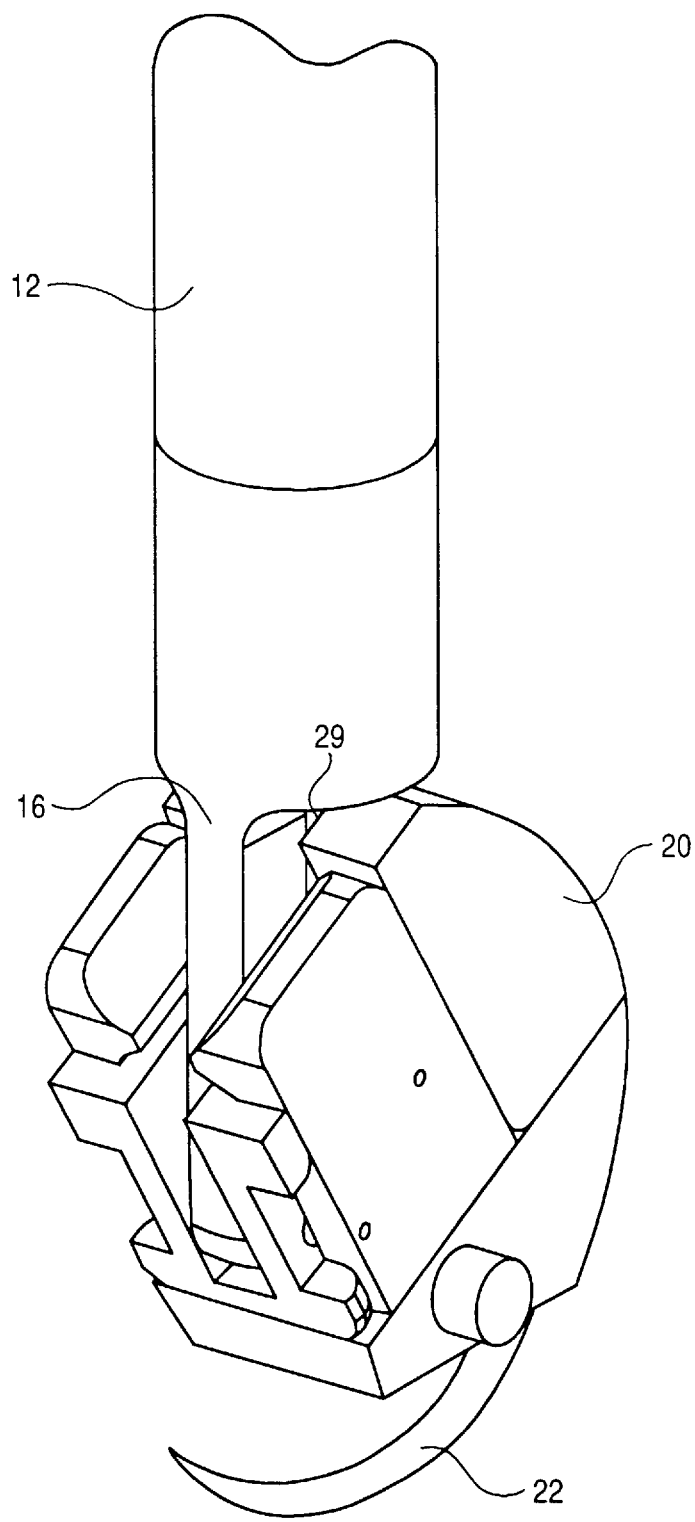
FIG. 2 is a more detailed view of the distal end of the suturing device of FIG. 1.

Referring now to FIGS. 1 and 2, an exemplary embodiment of a suture placement device 10 will be described. The suture device 10 includes an elongate shaft 12 having a proximal end 14 and distal end 16. Attached to the proximal end 14 is a handle assembly 18 having a button 28 for pivoting a needle carriage 20 at the distal end 16 of the shaft 12. Removably held by the carriage 20 is a curved needle 22. Trailing the curved needle 22 is a length of suture 24 which has a second curved needle 26 at its opposite end. A suture holder 25 is slidably mounted to shaft 12. As best shown in FIG. 1A, suture holder 25 includes a slit 27 into which suture 24 may be placed. Suture holder 25 will preferably be constructed of an elastomeric material with slit 27 configured to frictionally engage the suture and maintain it in tension between holder 25 and carriage 20. In this way, suture 24 may be held both in tension and close to shaft 12 so that the surgeon will not need to separately hold onto suture 24 when performing a procedure. When carriage 20 is pivoted, suture 24 will slide through slit 27 as needed.

Figure 6:
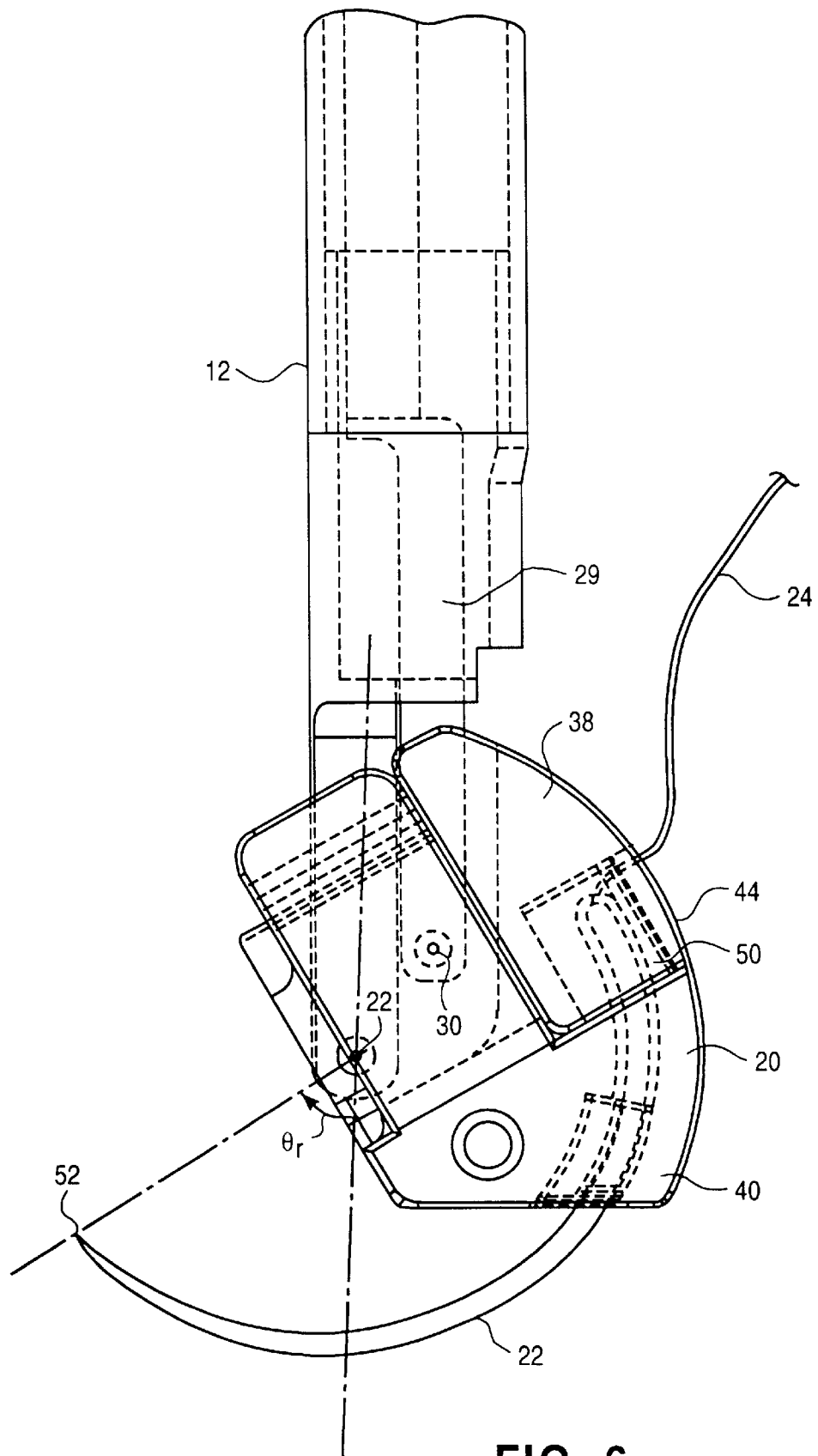
FIG. 6 illustrates a side view of the distal end of the suturing device of FIG. 1 showing the needle carriage in a retracted position.

As best shown in FIG. 6, the needle carriage 20 is pivotally connected to the distal end 16 of the shaft 12 by a pin 32. To pivot the carriage 20 about the pin 32, a rod 29 is slidable within shaft 12 and is attached at its distal end to the carriage 20 by a pin 30. The proximal end of the rod 29 is attached to the button 28 (see FIG. 3). In this manner, as the button 28 is translated back and forth, the rod 29 is axially translated to pivot the carriage about the pin 32.

Referring back to FIG. 1, the shaft 12 will preferably have a working length between handle assembly 18 and distal end 16 of at least 20 cm, and preferably 25 cm to 35 cm, so that the needle 22 may be placed at a desired location within a body cavity while the handle assembly 18 remains outside the patient. Shaft 12, carriage 20, and needle 22 are preferably configured to pass easily through a tubular space (such as a trocar sleeve or thoracic port) having an inner diameter of less than 30 mm, and preferably less than 12 mm. Shaft 12 and needle carriage 20 will preferably be configured to permit direct visualization of the needle 22 through the trocar when placing the needle 22 into tissue. The largest outer dimension of the shaft 12 and the needle carriage 20 (i.e. the width as measured perpendicular to the longitudinal axis of the shaft 12) will usually be less than about 30 mm, more preferably less than 20 mm, and most preferably less than 12 mm. The largest outer dimension of the suturing device will, however, depend upon the size and shape of needle 22, which will vary according to the type of procedure to be performed, the target tissue, and the anatomy and size of the patient.

As described in greater detail hereinafter, at least a portion of the needle carriage 20 will preferably be removably attached to the shaft 12 so that it may be replaced after use. The handle assembly 18 and shaft 12 will preferably be constructed of an autoclavable material, such as aluminum or stainless steel, so that the handle assembly 18 and shaft 12 may be reused after cleaning. The removable portion of carriage 20 will preferably be constructed of a disposable biocompatible material such as a medical grade plastic so that the carriage 20 may be discarded after use. Alternatively, handle assembly 18 and shaft 12 may also be constructed of a disposable biocompatible material so that the entire suturing device may be discarded after a procedure.

Figure 3:
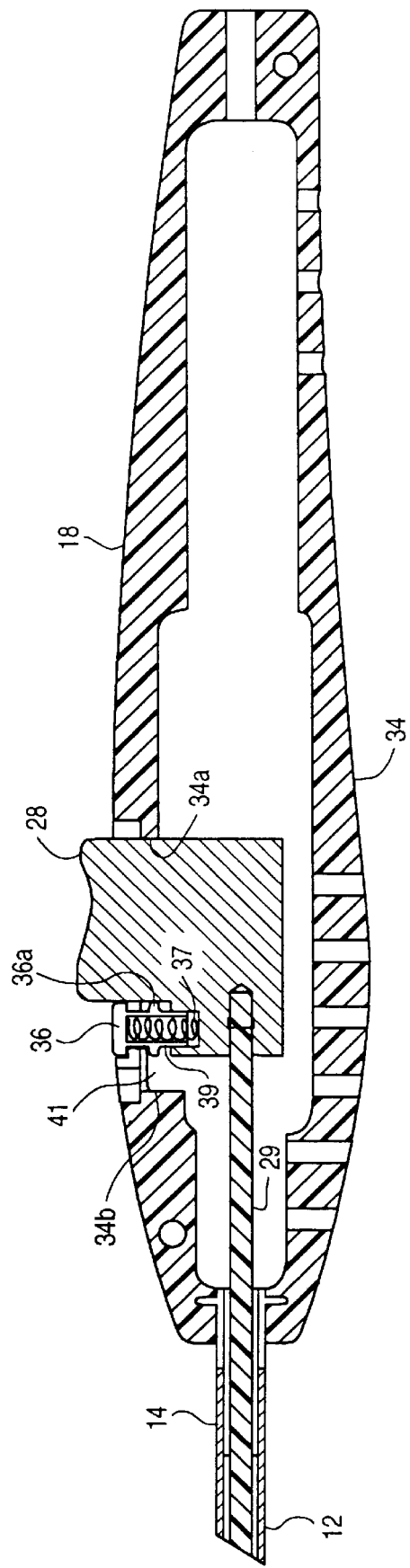
FIG. 3 illustrates a cross-sectional side view of a handle assembly of the suturing device of FIG. 1.

Referring to FIG. 3, the handle assembly 18 will be described in greater detail. The handle assembly 18 includes a housing 34 that is attached to the proximal end 14 of the shaft 12. Extending through the shaft 12 and into the housing 34 is the rod 29. The rod 29 is attached to the button 28 within the housing 34. In this way, translation of the button 28 translates the rod 29 through the shaft 12. A lock 36 may optionally be provided to prevent translation of the button 28 and rod 29 after button 28 has been distally advanced to drive the needle through tissue. Lock 36 rests within a notch 37 in button 28 and includes a lock flange 36a and an internal spring 39 which upwardly biases lock flange 36a, i.e. away from notch,37. When button 28 is distally translated to place needle carriage 20 in its fully deployed position, spring 39 forces lock flange 36a into a lock slot 41 in housing 34 to lock the needle carriage in place. To release the needle carriage from its locked position, lock 36 is depressed into notch 37 to remove lock flange 36a from lock slot 41. Button 28 is then proximally translated to move lock flange 36a to a position proximal of lock slot 41. Stops 34a and 34b of housing 34 control the amount of proximal and distal translation of the button 28 which in turn controls the amount of pivoting of the needle carriage 20 and rotation or movement of the needle 22.

It will be appreciated that alternative actuation mechanisms may be employed to pivot needle carriage 20. For example, button 28 may be replaced with a trigger which is pivotally attached to housing 34. In this way, squeezing of the trigger will cause needle carriage 20 to pivot.

Figure 4:
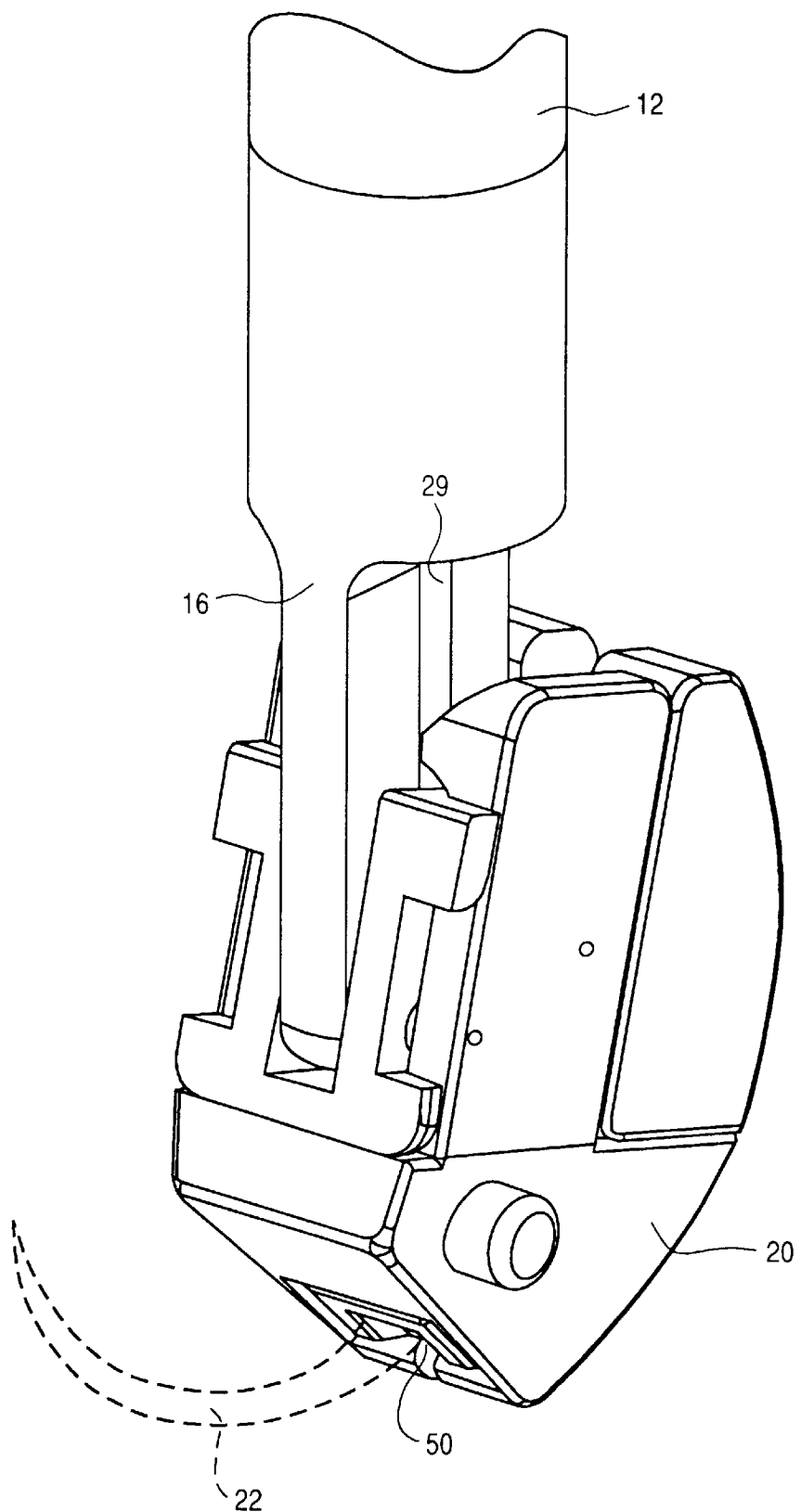
FIG. 4 illustrates a perspective view of a needle carriage at the distal end of the suturing device of FIG. 1.
Figure 5:
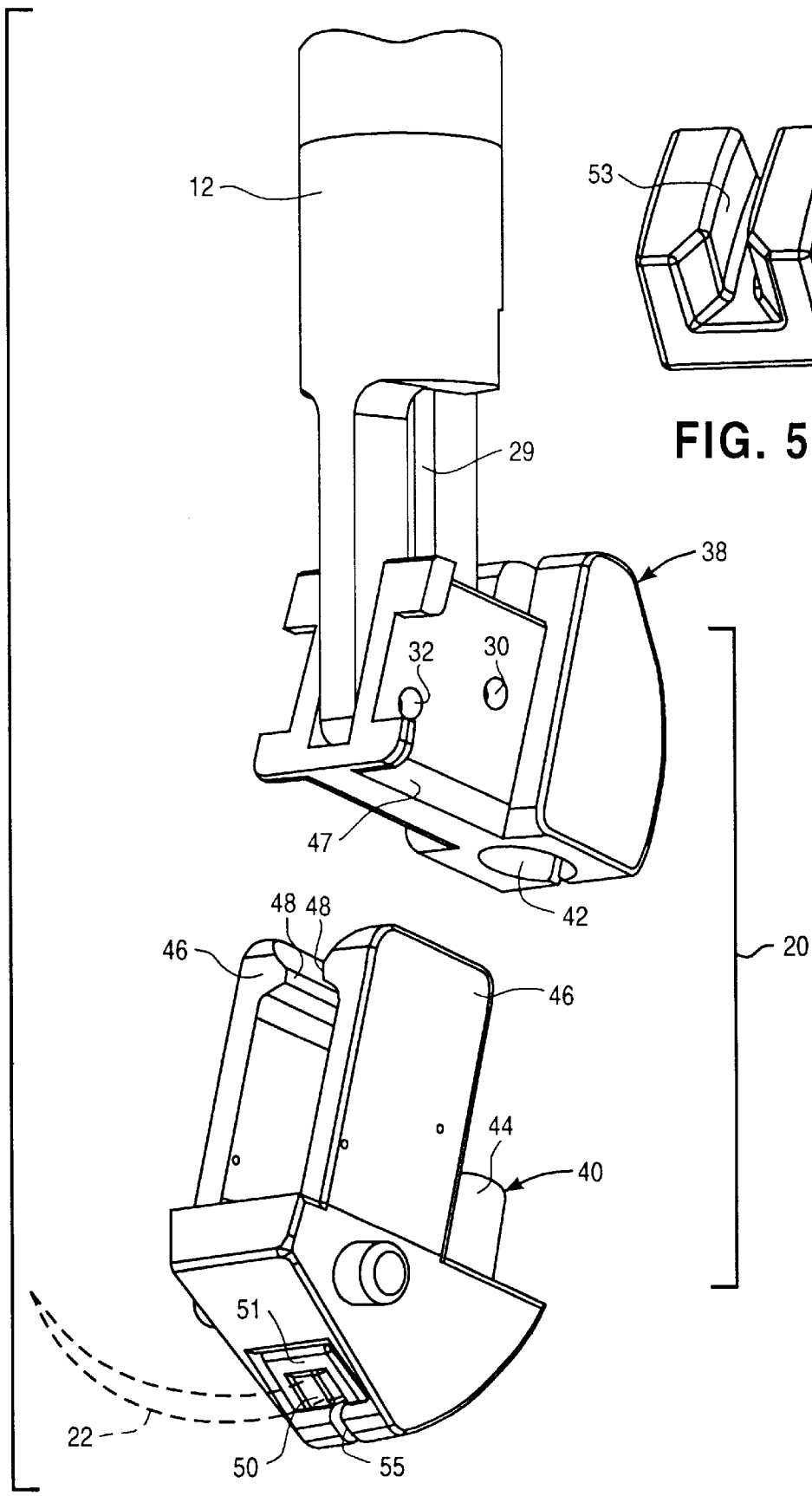
FIG. 5 illustrates removal of a removable portion of the needle carriage of FIG. 4.

Referring to FIGS. 4 and 5, construction of the needle carriage 20 will be described in greater detail. As best shown in FIG. 5, the needle carriage 20 includes a fixed portion 38 that is pivotally attached to the rod 29 and shaft 12 and a removable portion 40. The fixed portion 38 includes a channel 42 for receiving an insert 44 on the removable portion 40. The removable portion includes a snap fitting comprising a pair of resilient, deflectable tabs 46 which are received over a neck 47 on fixed portion 38 when the fixed and removable portions are connected together. Each tab 46 includes a catch 48 which snaps around neck 47 to secure portions 38 and 40 together.

The needle 22 is removably held within an elongate slot 50 in removable portion 40. An elastomeric insert 51 is positioned within slot 50 to hold needle 22 in place. As shown in FIG. 5A, insert 51 includes a channel 53 which receives needle 22. Channel 53 is preferably sized to be smaller than needle 22 so that the resilience of insert 51 may hold needle 22 in place. After needle 22 has been introduced through tissue, the needle 22 may be pulled from slot 50 by applying a sufficient force to slide the needle 22 from insert 51. The slot 50 includes a narrow portion 55 through which the suture 24 may be removed from the carriage 20 after the needle 22 has been removed.

Advantageously, the removable portion 40 may be separated from the suture device 10 and discarded following a procedure. Removable portion 40 is preferably constructed of a rigid biocompatible plastic such as polycarbonate, ABS, polysulfone, or the like. After the first removable portion 40 is removed, another removable portion 40 may then be attached to the fixed portion 38 and the device 10 reused. The replacement removable portion 40 may carry the same size and configuration of needles, or may alternatively have needles of different shapes or sizes. In another particularly preferable aspect, the slot 50 (or insert 51) may be appropriately shaped and sized to hold different shapes and sizes of needles. For example, needle 22 may be semicircular, elliptically curved, partially straight, ski-shaped, angular, or completely straight, and may be of various sizes, such as those having a radius of curvature of 5.6 mm, 6.3 mm, or 7.4 mm (such as those commercially available from Deknatel or Ethicon), with diameters of 0.3 mm to 0.8 mm. When arcuate, the needle will preferably have a length sufficient to have the needle form at least a quarter circle or greater. Further, the needle can be fashioned into at least two detachable parts, e.g. a tip portion and a shaft portion. With such a configuration, the tip may be grasped after passing through tissue and removed from the shaft.

The suture device 10 may be used with a variety of different types of needles by simply removing the portion 40 and attaching another portion 40 having a different type or size of needle. Optionally, the needle carriage 20 may be configured to hold more than a single needle at a time so that a plurality of needles may be placed into tissue at the same time. For example, a second slot parallel to slot 50 may be provided so that two needles interconnected by a length of suture may be mounted side-by-side in parallel on needle carriage 20 for placing a mattress stitch in tissue, as described in U.S. Pat. No. 5,571,215, the disclosure of which has been incorporated herein by reference.

Figure 7:
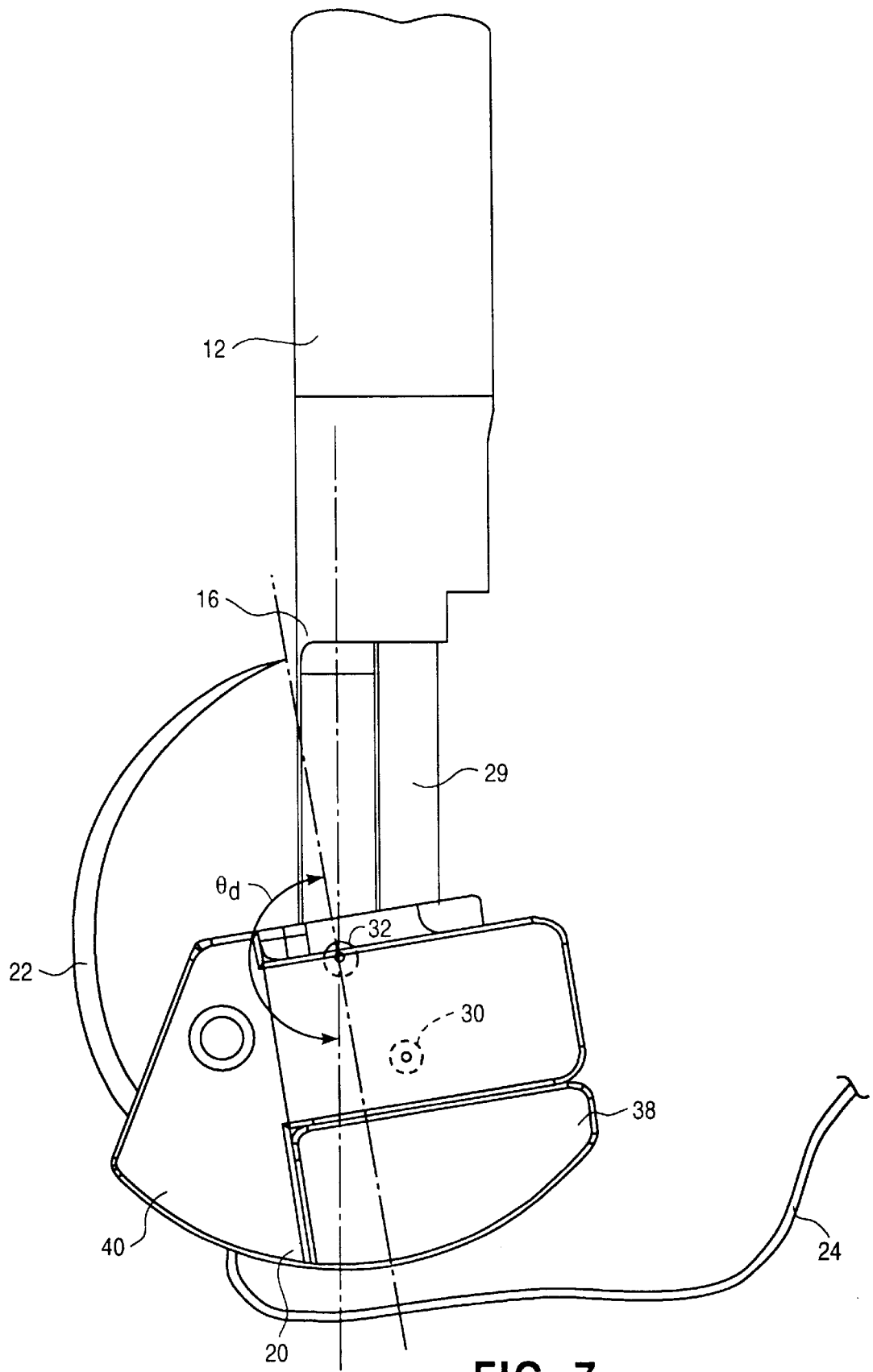
FIG. 7 illustrates rotation of the needle carriage of FIG. 6 to a fully deployed position.
Figure 8:
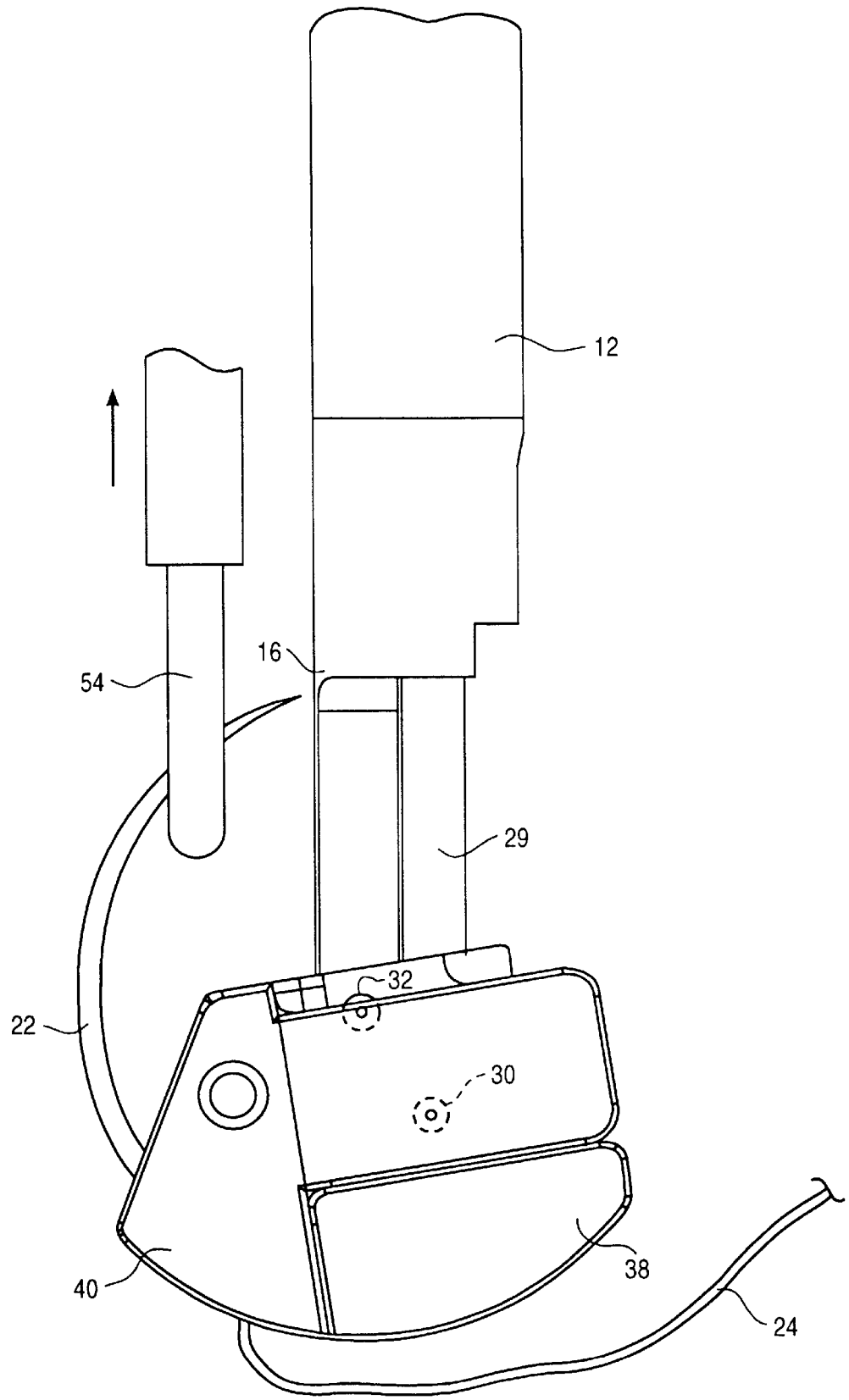
FIG. 8 illustrates removal of the needle from the needle assembly of FIG. 7 with a grasping mechanism.

Referring now to FIGS. 6–8, operation of the device 10 to rotate the needle 22 will be described in greater detail. As previously described, the needle carriage 20 is pivotally connected to the shaft 12 by pin 32, and the rod 29 is pivotally attached to the needle carriage 20 by pin 30 so that as the rod 29 is axially translated, the needle carriage 20 pivots about pin 32. In FIG. 6, the needle carriage 20 is in a retracted position. As the button 28 on handle assembly 18 is distally translated, the rod 29 is also distally translated to pivot the carriage 20 about the pin 32 as illustrated in FIG. 7. Pivoting of the carriage 20 will usually proceed until the needle 22 reaches or closely approaches the lateral side of the shaft 12. The needle 22 is thus directed back toward the shaft 12 into the deployed position of FIG. 7.

In one particularly preferable aspect, the radial distance from the pin 32 to the needle 22 will be substantially the same as the radius of curvature of the needle 22. In other words, the needle 22 is mounted so that its center of curvature lies on pin 32, its center of rotation on carriage 20. In this way, the needle 22 is passed through an arc having substantially the same radius as the radius of curvature of the needle 22. Such movement facilitates the passing of the curved needle 22 through tissue with minimum frictional resistance. Preferably, the needle will have a radius of curvature of about 2 mm to 11 mm, and more preferably from about 5.5 mm to 7.5 mm for procedures involving suture placement in or around the annulus of a heart valve. In this way, needle 22 may be rotated through a relatively large arc with minimal or no lateral movement of the shaft 12, allowing the needle 22 to obtain a sufficient "bite" into the annulus or surrounding tissue to place the suture 24 well away from the edge of the annulus.

Preferably, carriage 20 is configured so that, in the retracted position of FIG. 6, sharp tip 52 of needle 22 is positioned such that a radial line drawn between pin 32 and sharp tip 52 is at an angle $\theta_r$ relative to the longitudinal axis of shaft 12 of between 0° and 90°, and preferably about 45° to 80°. Carriage 20 is preferably pivoted through an angle of at least about 90° into the deployed position of FIG. 7, wherein angle $\theta_d$ is between 90° and 180°, and preferably about 135° to 170°.

The carriage 20 will further preferably be rotatable within a plane parallel to the central axis of the shaft or within about 45° of that plane, and preferably within about 20° of the plane. Configuring the needle carriage 20 in this manner facilitates placement of the needle 22 through a layer of tissue that is lying perpendicular to shaft 12 such as the annulus of a heart valve which is accessed through an intercostal port. For example, the carriage 20 may be positioned through the center of the annulus, and the carriage 20 rotated to proximally advance the needle 22 into the annulus tissue with little or no axial or lateral movement of the shaft 12. After the sharp tip 52 of needle 22 has exited the annulus, the needle 22 may be pulled from the carriage 20 with a grasping instrument 54 as illustrated in FIG. 8. Grasping instrument 54 may be separate and independent from device 10 or may be coupled to shaft 12. Alternatively, other grasping instruments or needle catching devices may be employed to grasp the needle 22 and pull it from the carriage 20 as described in greater detail hereinafter.

Needle 22 is preferably mounted to carriage 20 at its proximal end so that a substantial part of the distal portion of the needle is exposed and visible. This provides the surgeon with the ability to poke the needle 22 into tissue, view the initial placement, withdraw the needle 22, and redirect the needle 22 into the tissue at a different location. In this way, the surgeon can precisely place the needle 22 at the desired location in an easy and convenient manner. Once the desired location has been obtained, the button 28 may be further translated to further direct the needle 22 through the tissue.

The pivotal attachment of the needle carriage 20 to the shaft 12 at pin 32 will preferably be offset from the central axis of the shaft 12 to facilitate visualization of needle 22 when viewing the needle 22 (and particularly placement of the sharpened tip 52) from the proximal end of the device. Optionally, the shaft 12 may be articulated, angled, L-shaped or curved laterally to further facilitate direct visualization of the needle 22 through an intercostal port.

Although shown with a needle that is curved in a circular arc, the carriage 20 can be configured to hold needles having different geometric configurations. For example, the needle may have a straight proximal portion and a curved portion near its sharp tip so that the needle has a configuration similar to an alpine ski. Preferably, carriage 20 will be configured to move the curved portion of such a needle through tissue in an arc conforming to the arc of the curved portion and the straight portion will be passed in a straight path through the tissue.

Figure 9A:
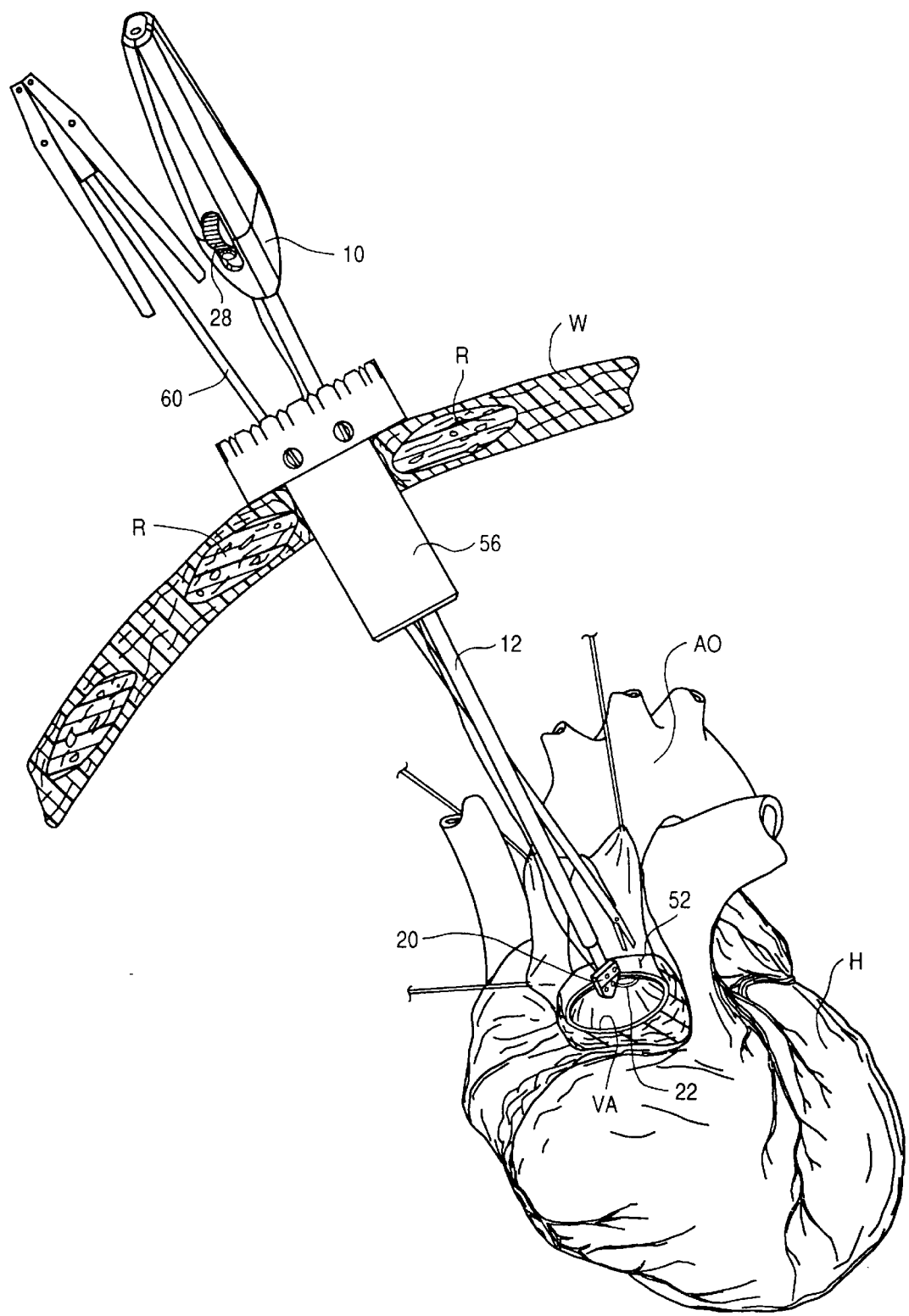
FIGS. 9A and 9B illustrate an exemplary method for placing a suture in the annulus of a heart valve using the suturing device of FIG. 1 according to the present invention.
Figure 9B:
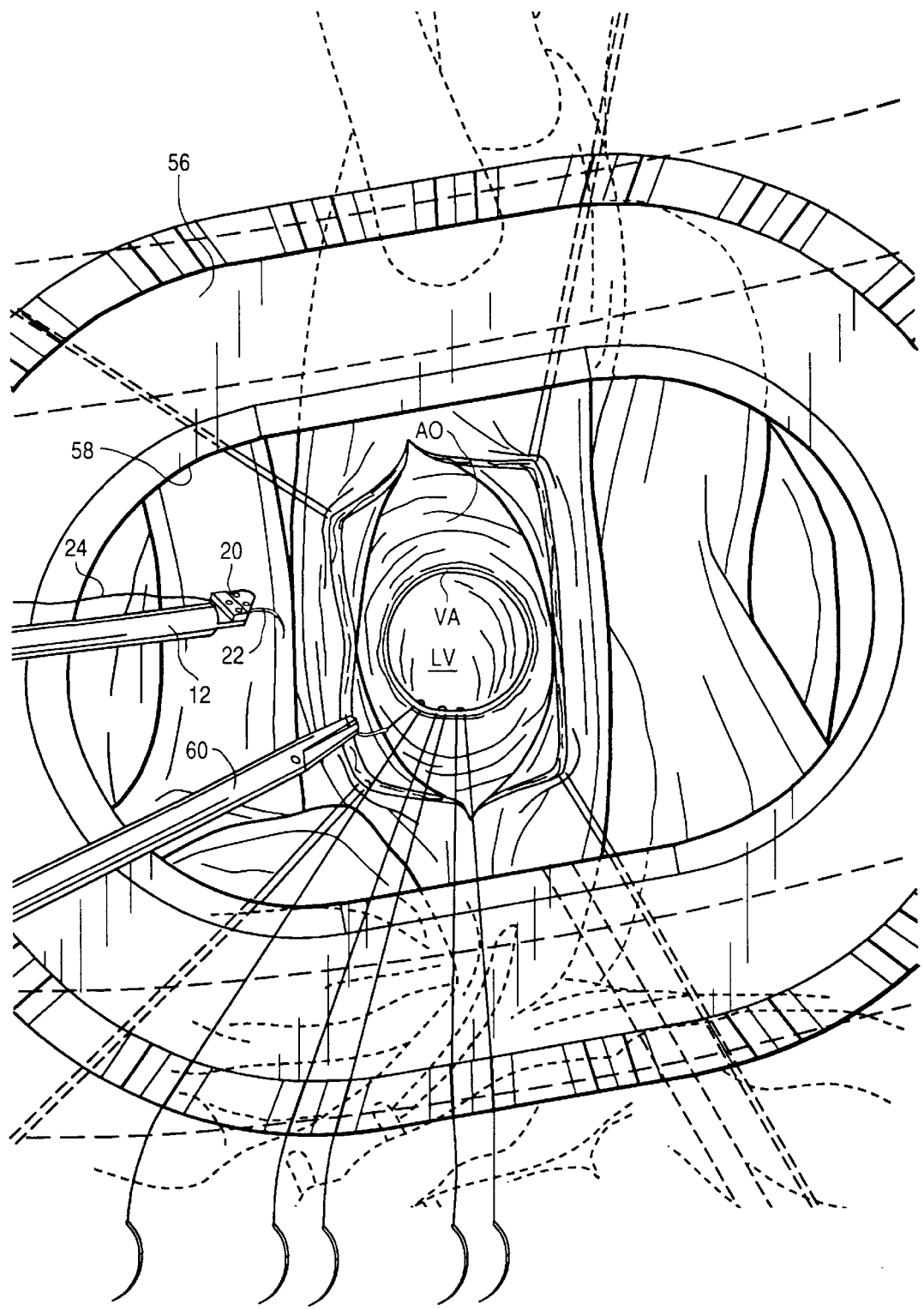

Referring now to FIGS. 9A and 9B, operation of the suture device 10 to place a suture in the valve annulus VA of the aortic valve will be described in greater detail. The suture device of the invention is equally useful in other procedures, including repair and replacement of the mitral, tricuspid, and pulmonary valves using the techniques described in U.S. Pat. No. 5,571,215, which has been incorporated herein by reference. Access to the thoracic cavity is obtained through a trocar 56 disposed between two adjacent ribs R in chest wall W via a percutaneous intercostal penetration. The terms "percutaneous intercostal penetration", "intercostal penetration", and "intercostal port" as used herein refer to a penetration, in the form of a small cut, incision, hole, cannula, trocar sleeve, or the like, through the chest wall between two adjacent ribs, wherein the patient's rib cage and sternum remain substantially intact, without cutting, removing, or significantly displacing the ribs or sternum. These terms are intended to distinguish a gross thoracotomy such as a median sternotomy, wherein the sternum and/or one or more ribs are cut or removed from the rib cage, or one or more ribs are retracted significantly, to create a large opening into the thoracic cavity. A "percutaneous intercostal penetration" may abut or overlap the adjacent ribs between which it is formed, but the maximum width of the penetration which is available for introduction of instruments, prostheses and the like into the thoracic cavity will be the width of the intercostal space, bounded by two adjacent ribs in their natural, substantially undeflected positions. It should be understood that one or more ribs may be retracted or deflected a small amount without departing from the scope of the invention; however, the invention specifically seeks to avoid the pain, trauma, and complications which result from the large deflection or cutting of the ribs in conventional, open-chest techniques.

Entry into the interior of the aorta A and removal of the aortic valve is described in copending application Ser. No. 08/594,870, entitled, "Less-Invasive Devices and Methods for Cardiac Valve Surgery", Attorney Docket No. 14635-52, which is incorporated herein by reference. With the aortic valve removed, a prosthetic replacement valve may be sutured to tissue in or adjacent to the patient's natural valve annulus VA. To place the sutures in the valve annulus VA, the suture device 10 is inserted into the thoracic cavity through the trocar 56 as illustrated in FIG. 9A. A double armed suture is utilized with a length sufficient to allow both ends to be withdrawn from the body cavity from the valve annulus. A needle 22 on one end of the suture is held in needle carriage 20. The suture device 10 is distally advanced into the aorta AO while the needle carriage 20 is in the retracted position of FIG. 6 until the sharp tip 52 of the needle 22 passes distally beyond the valve annulus VA into the left ventricle. At all times, the handle assembly 18 preferably remains outside the patient so that the button 28 may be operated from outside of the patient to pivot the carriage 20 as previously described.

Under direct visualization through a second trocar or through trocar 56 and/or by video-based visualization using an endoscope positioned through a trocar, the needle carriage 20 is pivoted about the shaft 12 to poke the sharpened tip 56 into the valve annulus VA. The curved geometry of the needle 22 and the pivotal attachment of the carriage 20 allow for the sharpened tip 52 to be poked well into the annulus VA so that a sufficient "bite" may be obtained, even when lateral movement of the shaft 12 is limited by the size of the passage 58. Preferably, the needle 22 will be rotated about its own arc as it is driven through the tissue. In this way, the needle 22 may be advanced through the tissue with minimal resistive force.

After the needle 22 is initially poked through the valve annulus VA, the surgeon is able to visualize exit of the sharpened tip 52, preferably by direct visualization through the trocar 56. In the event that the sharpened tip 52 is initially misplaced, the surgeon may move button 28 proximally to retract the needle 22 from the valve annulus VA and attempt another poke into the valve annulus VA at another location. Once proper placement is determined, the button 28 is fully translated to drive the needle 22 through the valve annulus VA and back toward the shaft 12.

As illustrated in FIG. 9B, forceps 60 may then be introduced through the trocar 56 or through a second trocar and employed to grasp the needle 22 and to pull it from the needle carriage 20 and then completely through the valve annulus VA. Alternatively, the suture device 10 may include an integral needle catch to capture and remove the needle 22 as described in alternative embodiments hereinafter. After being applied to the valve annulus VA, the suture 24 is withdrawn from the thoracic cavity through passage 58 of the trocar 56. A similar procedure is followed to drive the second needle 26 (not shown) that is attached to the opposite end of the suture 24 through the valve annulus VA. When withdrawn from the thoracic cavity, the suture 24 may be placed in slots of an organizing ring, and the replacement valve sutured in place as described in U.S. Pat. No. 5,571,215, previously incorporated by reference.

Figure 10A:
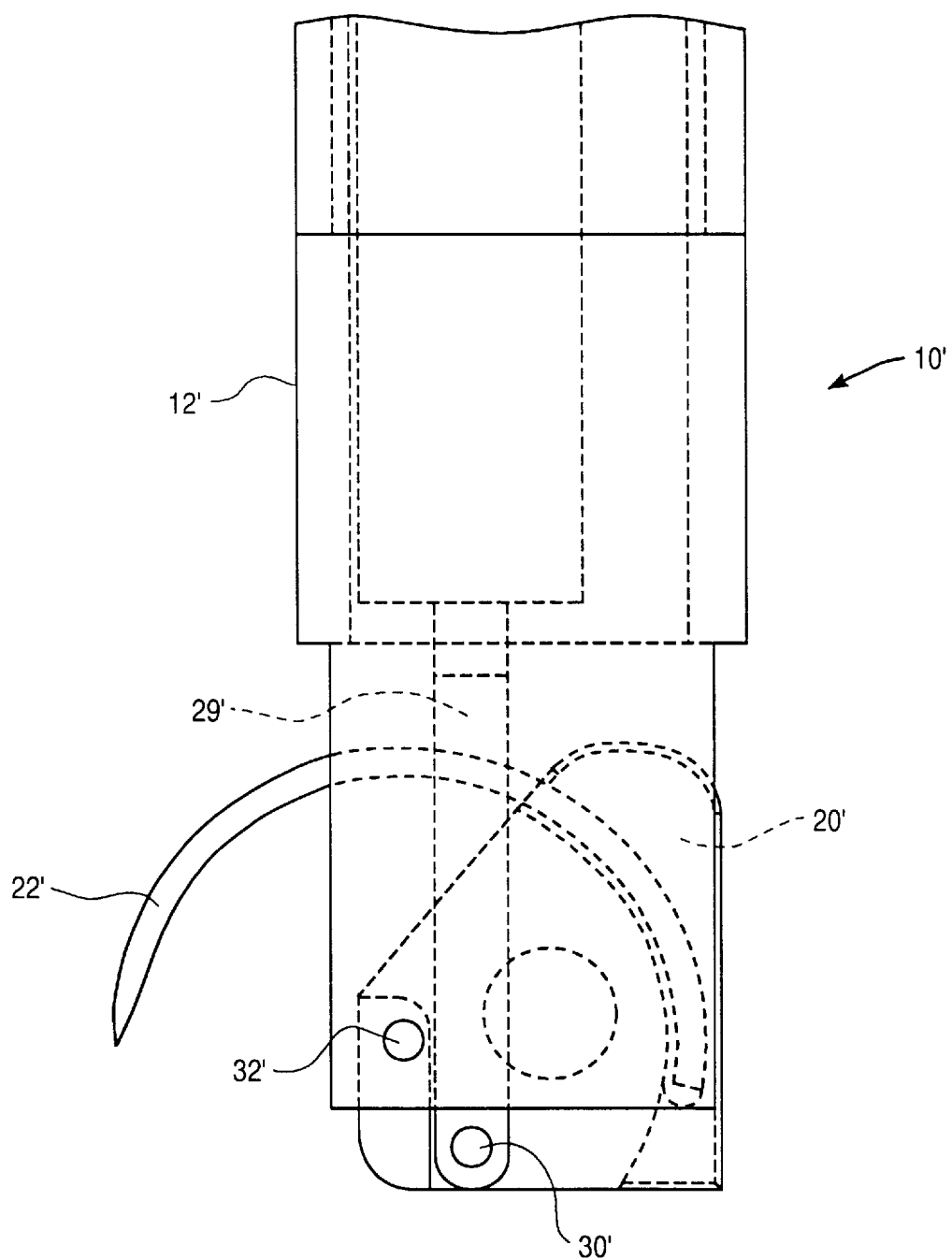
FIGS. 10A and 10B illustrate an alternative embodiment of a suturing device having a needle carriage which rotates a needle downward and away from the shaft.
Figure 10B:
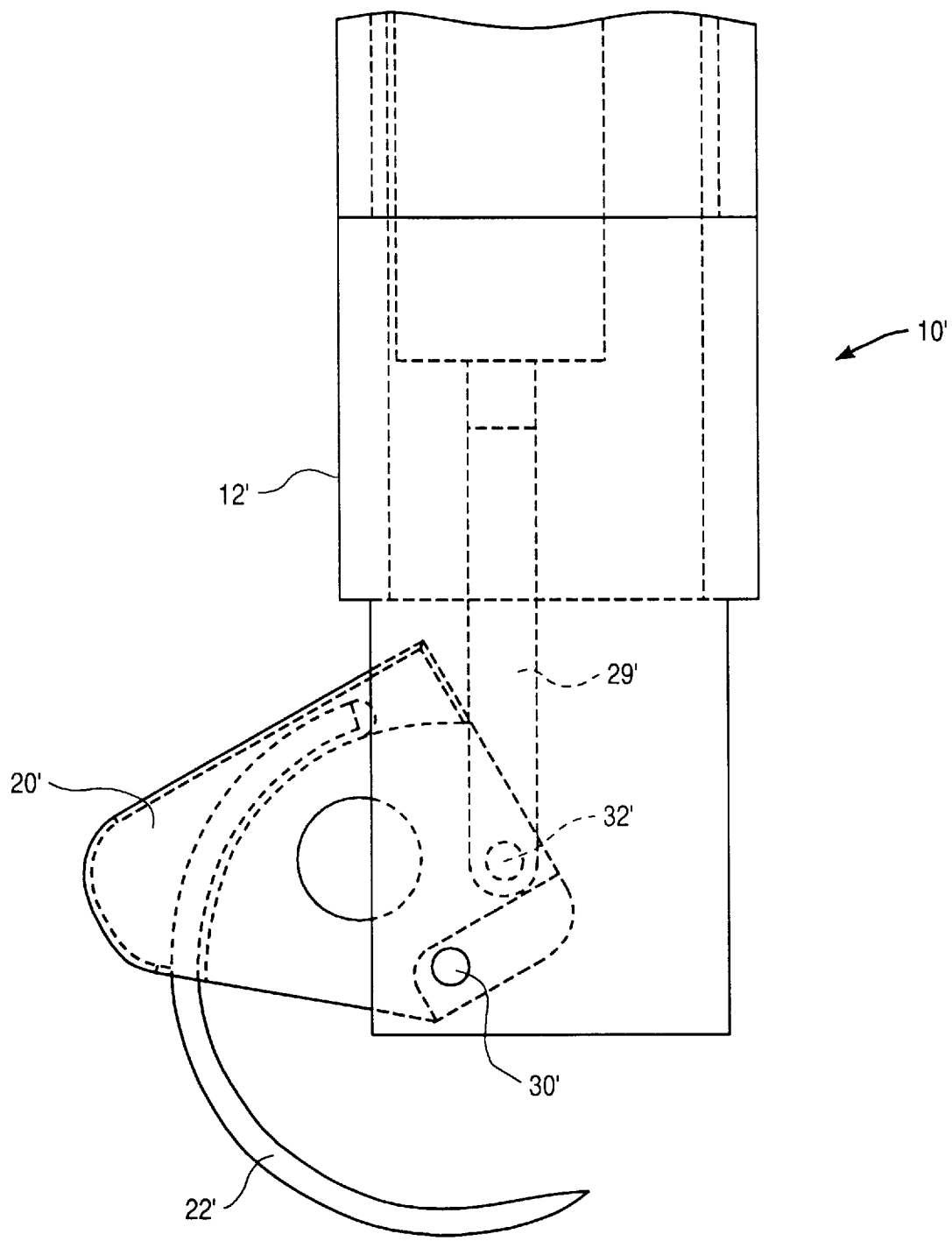

Although the suture device 10 has been described in the context of placing a suture in the valve annulus VA by passing the needle 22 from the left ventricle to the aorta, the suture device 10 could be modified to drive the needle 22 from the aorta to the left ventricle. For example, the needle carriage 20 could be modified to hold the needle 22 so that its sharpened tip is moved distally and away from the shaft 12. An example of such an embodiment is illustrated in FIGS. 10A and 10B. In FIG. 10A, a suture placement device 10' includes a shaft 12' having a rod 29' extending therethrough. Rod 29' is operably connected to a needle carriage 20' by a pin 30', while needle carriage 20' is in turn operably connected to shaft 12' by a pin 32'. A needle 22' is removably held in needle carriage 20'. A handle assembly (not shown) which is similar to handle assembly 18 of FIG. 1 is employed to translate rod 29', which in turn pivots needle carriage 20' about pin 32'. Device 10' is shown in a fully retracted position in FIG. 10A. Upon distal translation of rod 29', needle 22' is moved distally and away from shaft 12' until reaching a fully deployed position as illustrated in FIG. 10B.

Needle carriage 20' may optionally be constructed so that it is interchangable with needle carriage 20 of FIG. 1. This may be accomplished by providing a removable attachment anywhere along shaft 12' so that a portion of shaft 12' and needle carriage 20' may be removed and replaced with a portion of shaft 12 and needle carriage 20. In this manner, the same handle and shaft (or a portion thereof) may be used with different needle carriage embodiments so that the device may be used to place suture going from the aorta to the left ventricle or from the left ventricle to the aorta.

Figure 11:
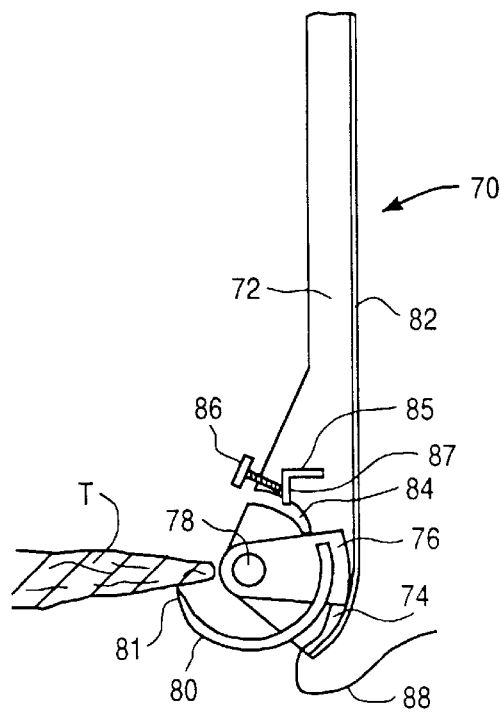
FIGS. 11 and 12 illustrate an alternative embodiment of a suturing device having a rotating semicircular needle and a fixed needle catch according to the present invention.
Figure 12:
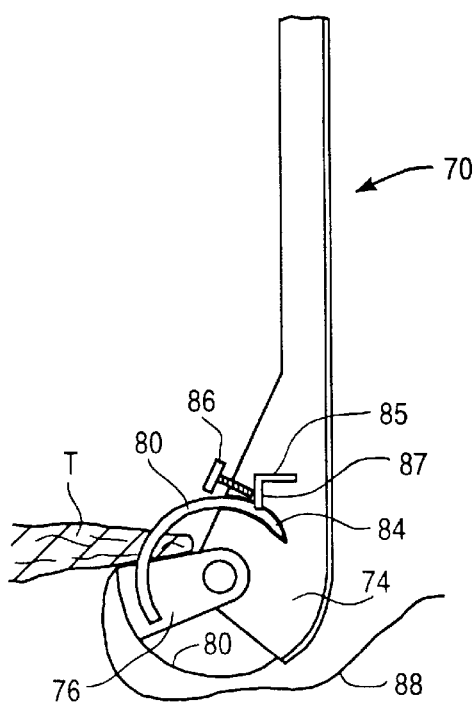

Referring to FIGS. 11 and 12, an alternative embodiment of a suture placement device 70 will be described. The suture device 70 includes an elongate shaft 72 having a proximal end (not shown) and a distal end 74. A needle holder 76 is pivotally attached to the shaft 72 at the distal end 74 by a pin 78. Removably held within the needle holder 76 is a needle 80. The needle 80 is curved and is semicircular in geometry. The needle 80 includes a sharpened tip 81 that is rotatable from a retracted position distal to pin 78 to a deployed position proximal to pin 78. A flexible rod 82 is provided to rotate the needle holder 76. A proximal end (not shown) of the rod 82 is connected to a handle assembly similar to the handle assembly 18 of the device 10 as previously described. The rod 82 is preferably constructed of a super elastic material, such as Nitinol™, so that the rod 82 may drive needle holder 76 in an arc when distally translated to pivot the needle holder 76 about the pin 78 as illustrated in FIG. 12. Preferably, the needle 80 will be radially spaced apart from the pin 78 by substantially the same distance as the radius of curvature of the needle 80 so that the needle 80 may be passed through an arc substantially conforming to the radius of the needle 80 as it passes through tissue T.

After passing through tissue T, the needle 80 enters a curved slot 84 in the shaft 72 which catches the distal end of needle 80. A leaf spring 85 is mounted to shaft 70 such that a free end 87 thereof extends into slot 84 to engage needle 80. A bolt 86 is provided to adjust the force of spring 85 against needle 80. The rod 82 is then proximally translated to reverse the direction of needle holder 76 and remove the needle 80 from the needle holder 76. The suture device 70 may then be proximally withdrawn with the needle 80 held in the slot 84 to pull a suture 88 through the tissue T. In this way, the suture device 70 is provided with an integral needle catch, thereby eliminating the need for a separate instrument to pull the needle 80 from the needle holder 76.

Figure 13:
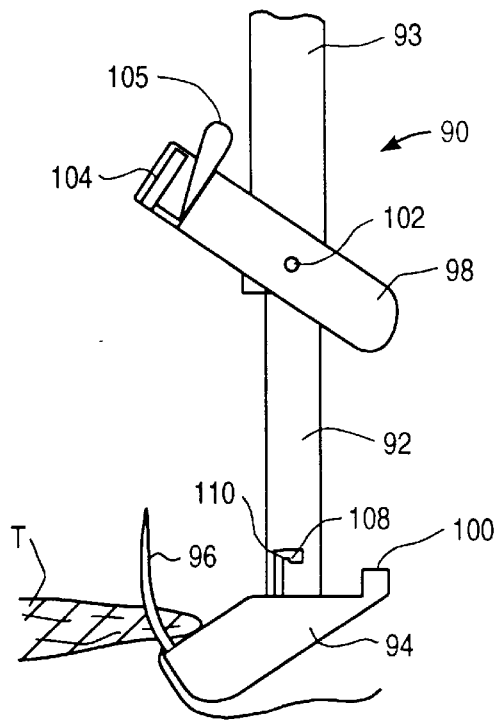
FIGS. 13 and 14 illustrate another alternative embodiment of a suturing device having a slightly curved needle that is held in a stationary needle holder and a swinging needle catch according to the present invention.
Figure 14:
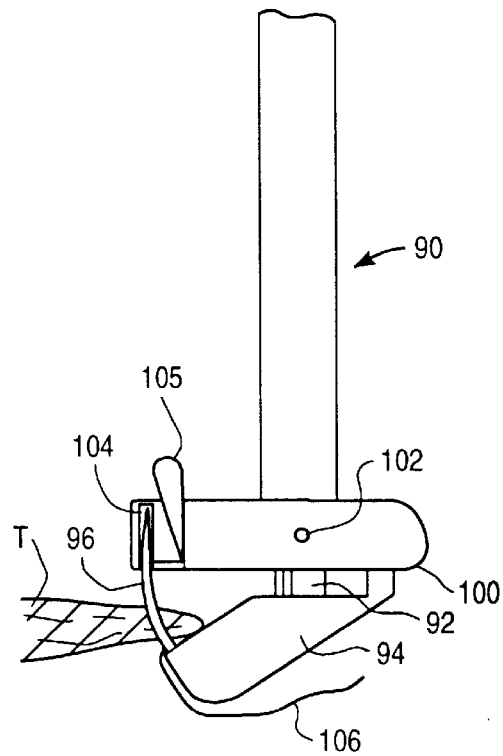
Figure 15:
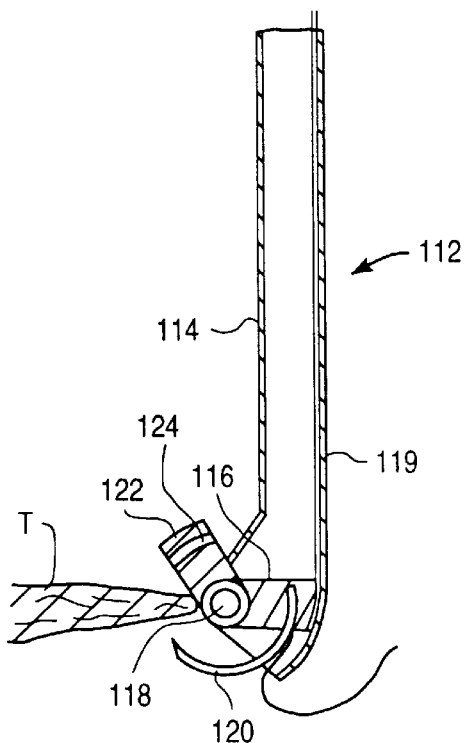
FIGS. 15–18 illustrate yet another alternative embodiment of a suturing device having a semicircle needle that is held in a rotating holder and a rotating tissue clamp/ needle catch according to the present invention.

A further alternative embodiment of a suture placement device 90 is shown in FIGS. 13 and 14. The suture device 90 includes an elongate shaft 92 having a needle holder 94 attached thereto. The needle holder 94 is configured to remain stationary relative to the shaft 92. Removably held within the needle holder 94 is a slightly curved needle 96 having a radius of curvature in the range from about 25 mm to 35 mm. To draw the needle 96 through tissue T, the needle 96 is proximally pulled through the tissue T by proximal translation of the shaft 92. An outer shaft 93 is slidable over shaft 92 and has a needle catch 98 pivotally mounted to its distal end. After needle 96 is passed through the tissue T, needle catch 98 is distally translated over the shaft 92 until engaging a stop 100 on the needle holder 94. The stop 100 causes the needle catch 98 to pivot about pin 102 until the needle 96 is received within a slot 104 in the needle catch 98 as illustrated in FIG. 14. A leaf spring 105 mounted to needle catch 98 engages needle 96 to retain it within slot 104. The needle catch 98 may then be proximally translated relative to the shaft 92 to pull the needle 96 from the needle holder 94 and to draw a suture 106 through the tissue T. In an exemplary embodiment, the needle holder 94 is removably attached to the shaft 92 by a pin 108 that is received in an L-shaped slot 110 in the shaft 92. In this way, the needle holder 94 may be removed from the shaft 92 and another needle holder 94 attached thereto to facilitate interchanging needles of various sizes and shapes.

Figure 16:
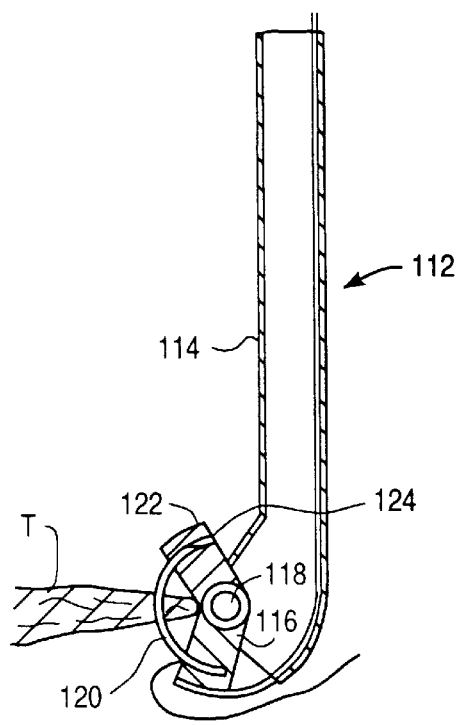

Referring to FIGS. 15–18, still another alternative embodiment of a suture placement device 112 will be described. The suture device 112 includes an elongate shaft 114 having a needle holder 116 attached to its distal end by a pin 118. A flexible rod 119 is used to pivot the needle holder 116 about the pin 118. A handle assembly (not shown) is at a proximal end of the shaft 114 for translating the rod 119 in a manner similar to the handle assembly of the device 10 as previously described. A semicircular needle 120 is removably held in the needle holder 116. The radius of the needle 120 is preferably substantially equal to the radial distance of the needle 120 from the pin 118 so that the needle 120 may be moved in an arc substantially conforming to the radius of the needle 120. The suture device 112 further includes a rotatable needle catch 122 that is pivotally attached to the shaft 114 by the pin 118. The needle catch 122 includes a slot 124 for receiving the sharpened tip of the needle 120 after passing through tissue as illustrated in FIG. 16. A leaf spring (not shown) like those of FIGS. 11–14 may be mounted to needle catch 122 to retain needle 120 in slot 124.

Figure 17:
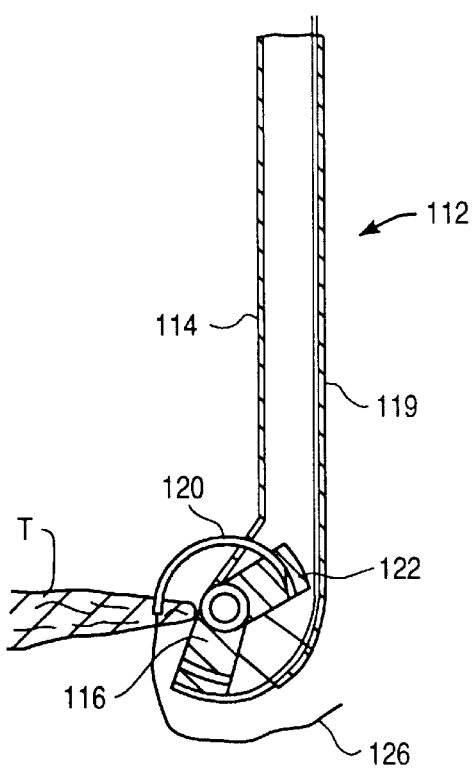
Figure 18:
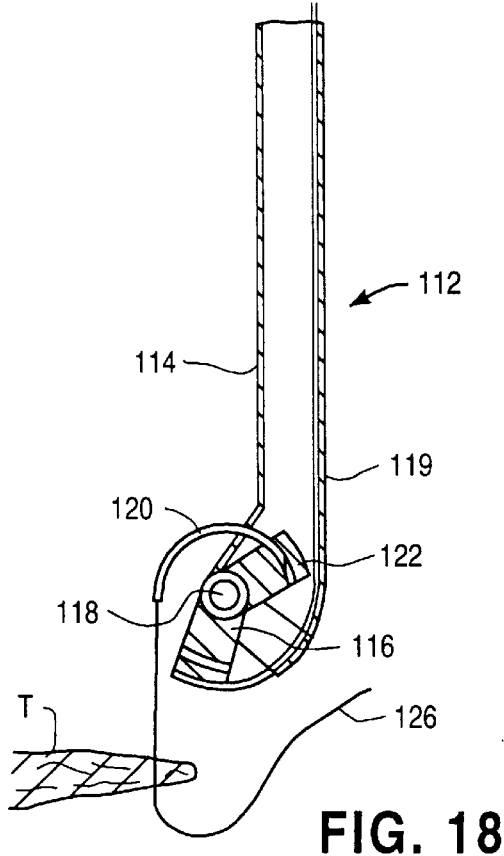

After the sharp tip of the needle 120 exits the tissue T and enters the slot 124, the needle holder 116 is further rotated to drive the needle 120 through the tissue T and move the catch 122 into the shaft 114 as illustrated in FIG. 17. A catch (not shown) may be provided within shaft 114 to engage needle catch 122 when it enters the shaft so as to retain it therein. The needle holder 116 is then pivoted in the opposite direction to remove the needle 120 from the needle holder 116. The suture device 120 may then be proximally withdrawn to pull a suture 126 through the tissue T and to remove the device 112 from the patient as illustrated in FIG. 18.

Referring to FIGS. 19–21, yet another alternative embodiment of a suture placement device 130 will be described. The suture device 130 includes an elongate shaft 132 having a needle holder 134 pivotally attached to its distal end. The suture device 130 operates in a manner similar to the suture device 90 of FIGS. 13 and 14 except that the needle holder 134 is pivotally attached to the shaft 132 by a pin 135. A slightly curved needle 136 is removably held by needle holder 134. A torsion spring 138 is provided to bias the needle holder 134 in a retracted position as illustrated in FIG. 19. In the retracted position, a line drawn from pin 135 to the sharpened tip 139 of the needle 136 will preferably be at an angle $\theta_r$ relative to the longitudinal axis of shaft 132 of about 0° to 90°, and preferably 30° to 75°. A needle catch 140 having a slot 142 is pivotally mounted to a tubular outer shaft 141 slidable over shaft 132. Upon distal translation of the needle catch 140, the needle catch 140 will engage a stop 144 on the needle holder 134 as illustrated in FIG. 20. The needle catch 140 is initially maintained in a non-pivoted orientation by a compression spring 146 which is stiffer than torsion spring 138. In this manner, as the needle catch 140 engages the stop 144, the needle holder 134 is pivoted about pin 138 to drive the needle 136 through the tissue T. At this point, a line drawn from pin 135 to the sharpened tip 139 of the needle will be at an angle of $\theta_d$ about 90° to 180°, preferably about 110° to 135°, relative to the central axis of the shaft 132. Further distal translation of the needle catch 140 causes the needle catch 140 to pivot about a pin 148 to drive the needle 136 into the slot 142 as illustrated in FIG. 21. A leaf spring 145 mounted to needle catch 140 retains needle 136 in slot 142. The needle catch 140 may then be proximally translated relative to the needle holder 134 to pull the needle 136 from the needle holder 134 and to pull a suture 150 through the tissue T. The suture device 130 may then be withdrawn from the patient.

Figure 22:
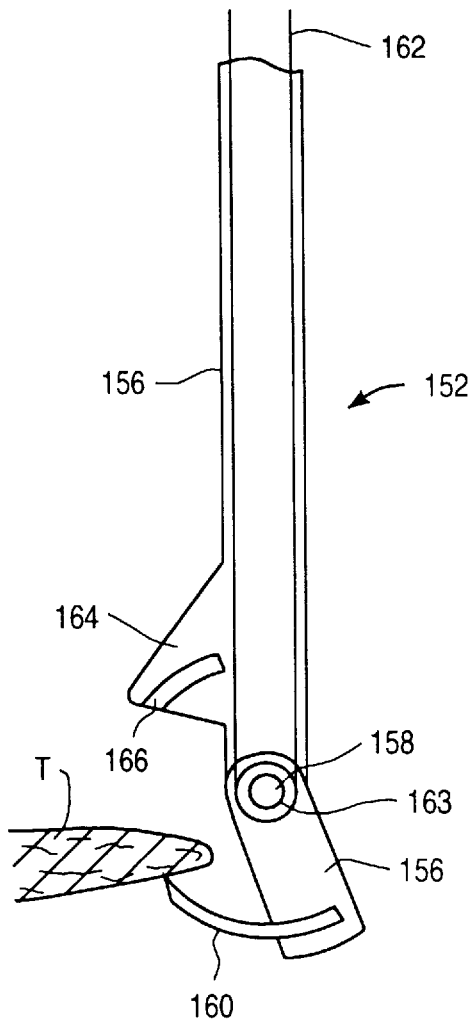
FIGS. 22 and 23 illustrate still a further alternative embodiment of a suturing device having a slightly curved needle that is held in a rotating needle holder and a fixed tissue clamp/needle catch according to the present invention.
Figure 23:
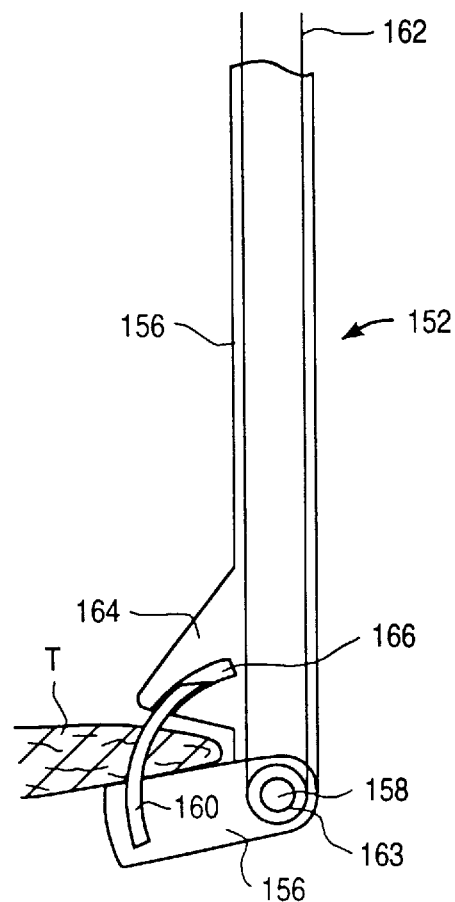

Another alternative embodiment of a suture placement device 152 is illustrated in FIGS. 22 and 23. The suture device 152 includes an elongate shaft 154 having a needle holder 156 pivotally attached to its distal end by a pin 158. A needle 160 having a radius of curvature in the range of about 25 mm to 35 mm is removably held in the needle holder 156. A flexible belt 162 is looped around a sheave or gear 163 mounted to needle holder 156 to allow the needle holder 156 to pivot about the pin 158 by translating belt 162. The shaft 154 further includes a stop 164 having a slot 166 for receiving the needle 160. The slot 166 is sized to receive the needle 160 with a friction fit so that the needle 160 will remain within the slot 166 after being placed therein. Alternatively, a leaf spring may be mounted to stop 164 to engage needle 160 as in previous embodiments. The stop 164 serves to maintain the position of the tissue T when the needle 160 is driven through it as illustrated in FIG. 23. After the needle 160 is received within the slot 166, the needle holder 156 may be rotated away from the stop 164 by reversing the direction of belt 162 to remove the needle 160 from the needle holder 156. The suture device 152 may then be proximally withdrawn with the needle 160 in the slot 166 to pull a length of suture through the tissue T.

Figure 24:
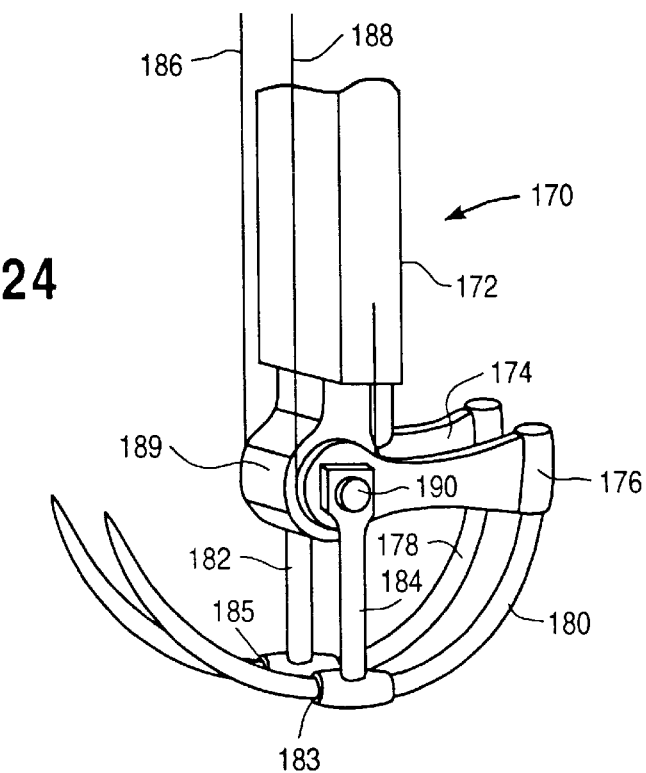
FIGS. 24–26 illustrate another alternative embodiment of a suturing device having a pair of semicircle needles and a pair of needle guides according to the present invention.
Figure 25:
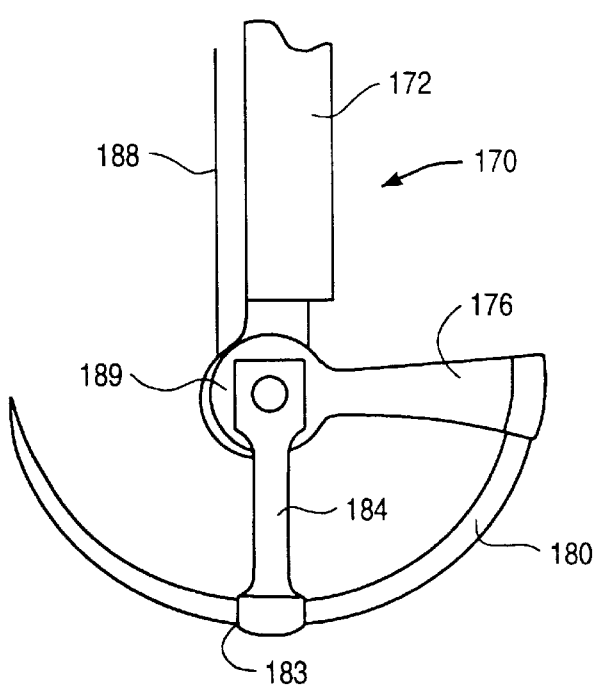
Figure 26:
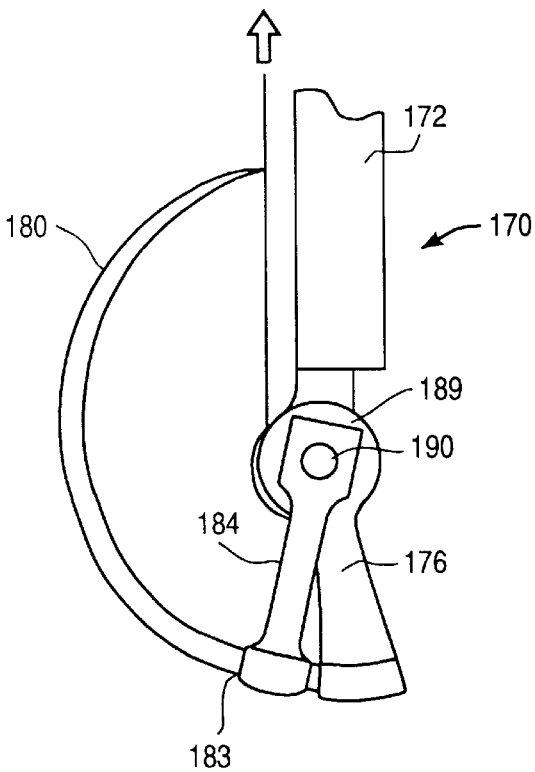

Still a further alternative embodiment of a suture placement device 170 is illustrated in FIGS. 24–26. The suture device 170 includes an elongate shaft 172 and a pair of needle holders 174 and 176 for removably holding a pair of needles 178 and 180. A pair of flexible belts 186 and 188 extend around sheaves 189 mounted to needle holders 174, 176 to rotate the needle holders 174, 176 about a pin 190. A pair of needle guides 182 and 184 having eyelets 183, 185 through which needles 178, 180 may slide may optionally be provided to assist in guiding the needles 178, 180 as they are driven by the needle holders 174, 176. Preferably, the length of the needle holders 174, 176 and the needle guides 182, 184 will be substantially the same as the radius of curvature of the needles 178, 180 so that the needles 178, 180 may be rotated in an arc substantially conforming to the curvature of the needles 178, 180. As the needle holders 174, 176 are pivoted about the pin 190, the sharpened tips of the needles 178, 180 are driven initially outwardly from the shaft 172, then back toward the shaft 172 as illustrated in FIG. 26. The needle guides 182, 184 may also be rotatable about the pin 190 so as not to interfere with the rotation of needle holders 174, 176. After passing through tissue, the needles 178, 180 may be pulled from the needle holders 174, 176 with a separate grasping instrument, such as needle graspers, or a needle catch may be provided on shaft 172 as in previous embodiments. Use of belts 186, 188 is further advantageous in that 360 degree rotation of needles 178, 180 is made possible depending on the extent of belt movement. In this way, sutures may be placed in tissue lying roughly perpendicular to the access port or incision, such as in the case of an aortotomy or atriotomy closure.

In an alternative embodiment, rotation of a needle carriage or a needle holder may be made possible by a pinion gear that is fixed to the needle carriage or holder. A rack is slidable within or along the shaft so that engagement of the rack with the pinion during translation will cause rotation of the needle carriage or holder.

Referring to FIG. 27, an alternative embodiment of a needle 192 will be described. The needle 192 may be utilized in any of the suture placement devices previously described herein. The needle 192 is hollow and includes an axial lumen 194 extending from an opening near a proximal end of the needle (not shown) to an exit hole 196 near the needle's sharpened tip. A length of suture 198 is prethreaded through the central lumen 194 and passes through the exit hole 196. In this way, the needle 192 is provided with a prethreaded length of suture 198 so that after the needle 192 is driven through tissue, the distal portion 197 of suture 198 extending through the exit hole 196 may be recovered. The needle 192 may then be withdrawn back through the tissue while distal portion 197 is held, so that suture 198 remains extending through the tissue. Alternatively, as illustrated in FIG. 28, the needle 192 may be passed through tissue without the length of suture 198 being prethreaded through the axial lumen 194. After passing through the tissue, the suture 198 may be introduced into the exit hole 196 and passed through the axial lumen 194. Optionally, suction may be applied to the proximal opening in axial lumen 194 to assist in drawing the suture 198 through the axial lumen 194. The distal portion of suture 198 remaining outside the hole 196 may then be secured while the needle 192 is withdrawn back through the tissue and until the needle 192 is removed from the suture 198.

A further alternative embodiment of a needle 200 that may be employed with the suture devices of the present invention is illustrated in FIG. 29A. The needle 200 is provided with a loop 202 of stainless steel wire, suture or other flexible material both ends of which are secured near the needle's sharpened tip. Usually, the loop 202 will be located about 1 mm to 3 mm from the sharpened tip. The loop 202 allows a length of suture 204 to be threaded therethrough as illustrated by arrow 206. In this manner, after the needle 200 is passed through tissue, the suture 204 may be threaded through the loop 202. The needle 200 may then be withdrawn back through the tissue to pull the suture 204 through the hole formed by the needle 200. The needle 200 may then be withdrawn from the patient and the suture 204 removed from the loop 200.

In FIG. 29B, an alternative embodiment of a needle 200' is shown. The needle has a central lumen 201 which terminates at a port 203 near the sharpened tip. A wire 207 extends through the lumen and is fashioned into a lasso 209 as it exits the port 203. In this manner, the suture 204 may be placed into the lasso 209 and the wire 207 pulled as shown to tighten the lasso 209 around the suture 204.

Figure 29C:
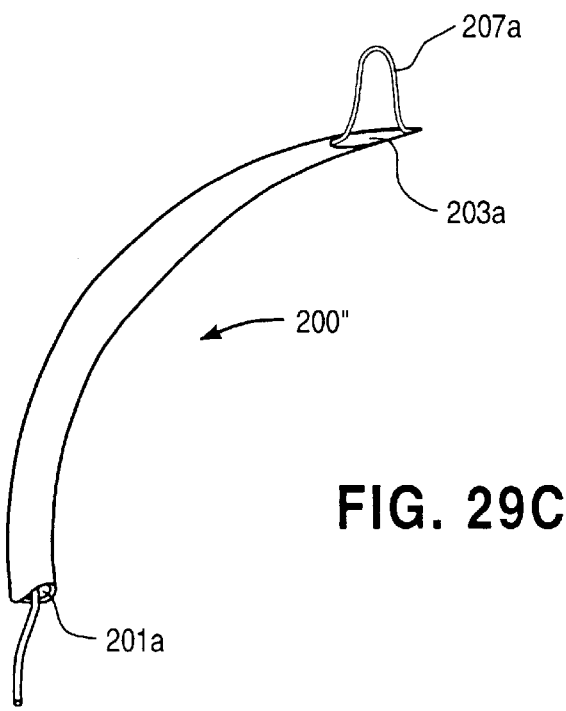
FIG. 29C illustrates still another embodiment of a needle having an opening at a distal end, with one end of a length of suture securely attached to the distal end.

FIG. 29C illustrates yet another alternative embodiment of a needle 200". Needle 200" is similar to needle 200' in that needle 200" includes a central lumen 201a which terminates in a distal opening 203a near the sharpened tip. A wire 207a extends through lumen 201a as has one end that is securely attached to needle 200" at or near the sharpened tip as shown. In this way, a loop may be formed at the sharpened tip as shown. To capture a length of suture, the free end of wire 207a is pulled to close the loop.

Figure 30A:
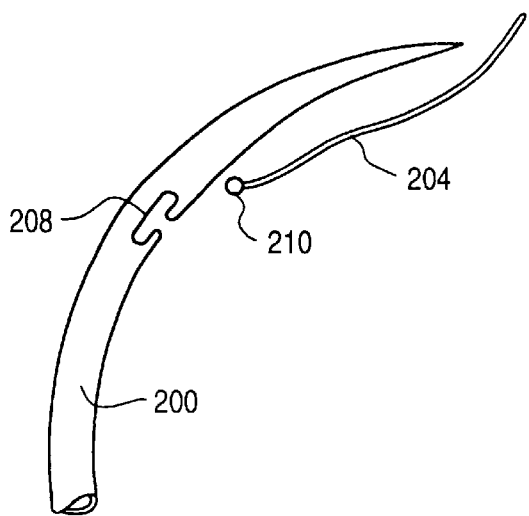
FIG. 30A illustrates yet another alternative embodiment of a needle having an anchor for receiving a ball on a suture according to the present invention.
Figure 30B:
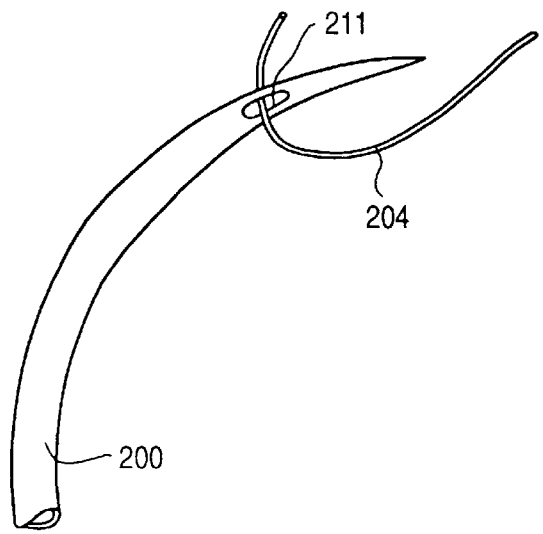
FIG. 30B illustrates a further alternative embodiment of a needle having an eyelet for receiving a length of suture according to the present invention.

Alternatively, as illustrated in FIG. 30A, the needle 200 may be provided with a slot 208 for receiving a ball 210 on the suture 204. Preferably, the slot 208 will be located about 1 mm to 3 mm from the sharpened tip. In this manner, the suture 204 may be attached to the needle 200 by engaging the ball 210 in the slot 208 after the needle 200 has passed through the tissue. Alternatively, the suture 204 may be attached to the needle 200 prior to passage of the needle 200 through tissue. After the needle has been directed through the tissue, the suture 204 may be removed from the needle 200 and the needle 200 withdrawn from the tissue as previously described. In another embodiment illustrated in FIG. 30B, the needle 200 may be provided with an eyelet 211 through which the suture 204 may be threaded.

Figure 31:
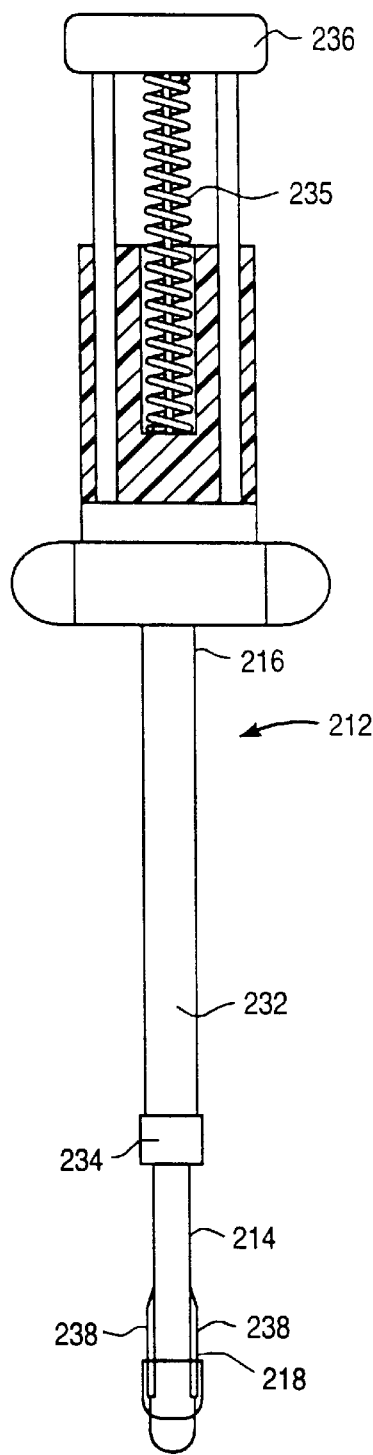
FIGS. 31–33 illustrate another alternative embodiment of a suturing device having a pair of straight needles attached to a stationary needle holder and a sliding needle catch according to the present invention.
Figure 32:
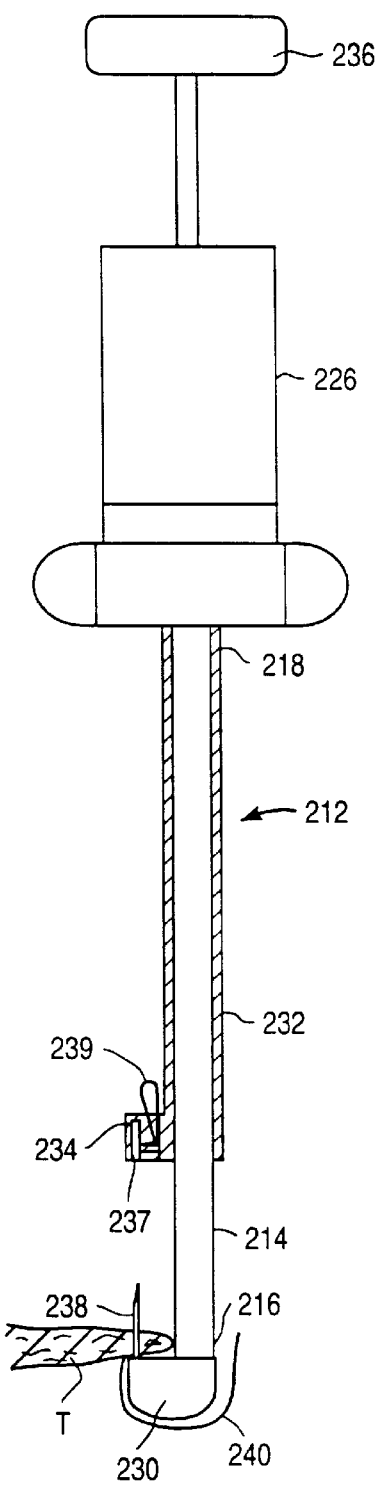
Figure 33:
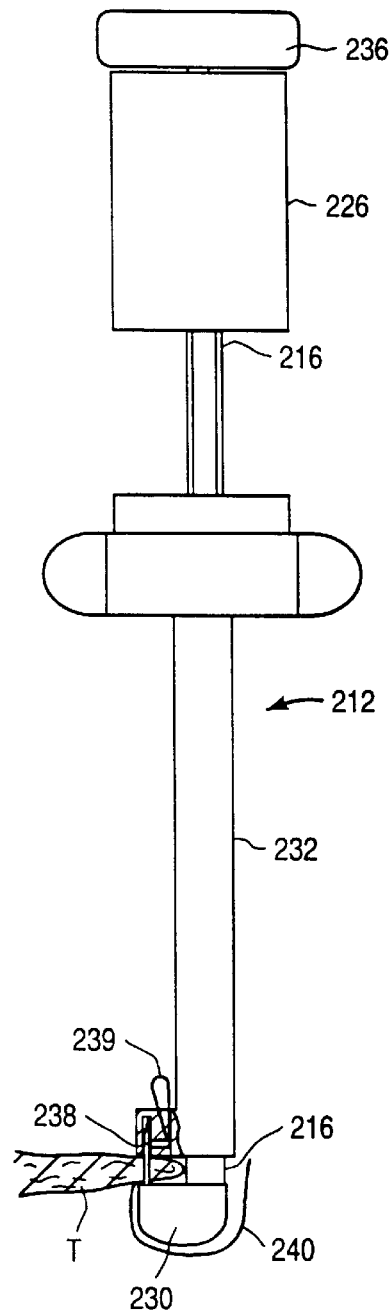

Referring now to FIGS. 31–35, other exemplary embodiments of suture placement devices having substantially straight needles will be described. Although described in a context of straight needles, such suturing devices may alternatively be provided with curved or semicurved needles as previously described. Referring now to FIGS. 31–33, one embodiment of a suture placement device 212 will be described. The suture device 212 includes an elongate shaft 214 having a proximal end 216 and a distal end 218. Secured to the proximal end 216 is a handle member 218. The distal end 216 of shaft 214 is attached to a needle carriage 230 in which a pair of needles 238 interconnected by a length of suture 240 are removably held.

The suture device 212 further includes an elongate sleeve 232 slidable over shaft 214 and having a needle catch 234 at its distal end. The sleeve 232 is attached to an actuator 236 slidably mounted to handle 226 and biased proximally by a compression spring 235. In this way, as the actuator 236 is distally translated, the sleeve 232 is also distally translated over the shaft 214 until the needle 238 is received in slot 237 in needle catch 234. A leaf spring 239 retains needle 238 in slot 237. The actuator 236 may then be proximally translated to proximally translate the sleeve 232 and pull the needle 238 from the needle carriage 230 with the needle 238 remaining in the catch 234. The suture device 212 may then be withdrawn from the patient with a length of suture 240 extending between needles 238 forming a mattress stitch in the tissue T.

Figure 34:
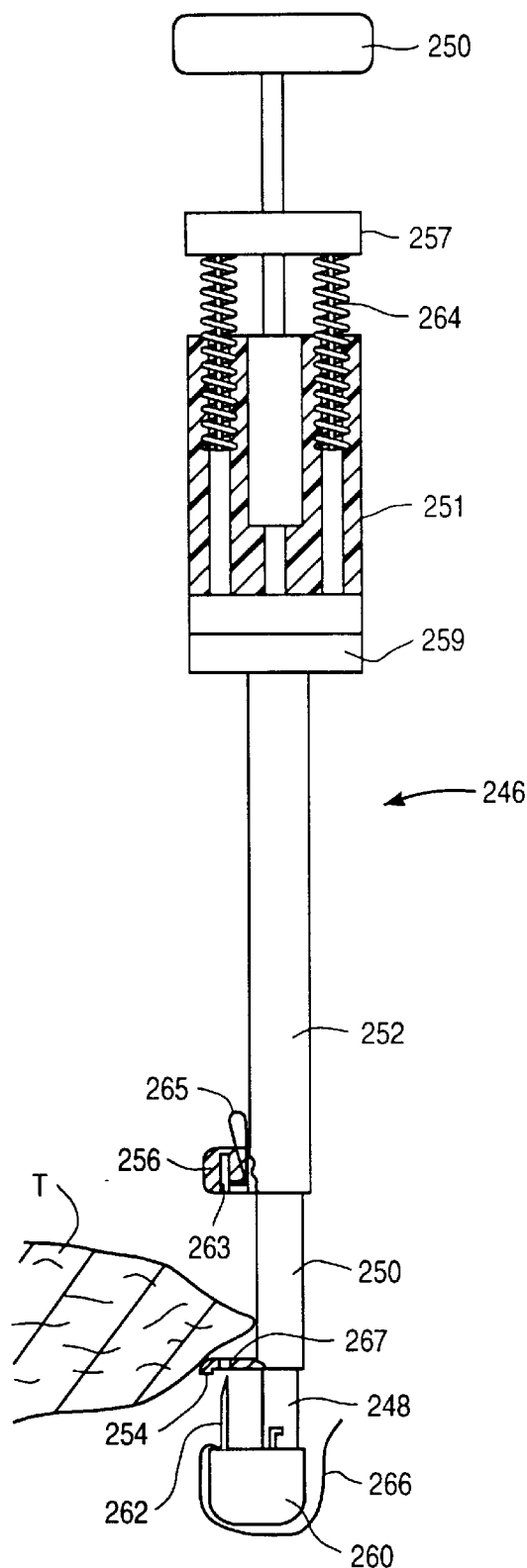
FIGS. 34 and 35 illustrate yet another alternative embodiment of a suturing device having a straight needle and a tissue clamp/needle catch according to the present invention.
Figure 35:
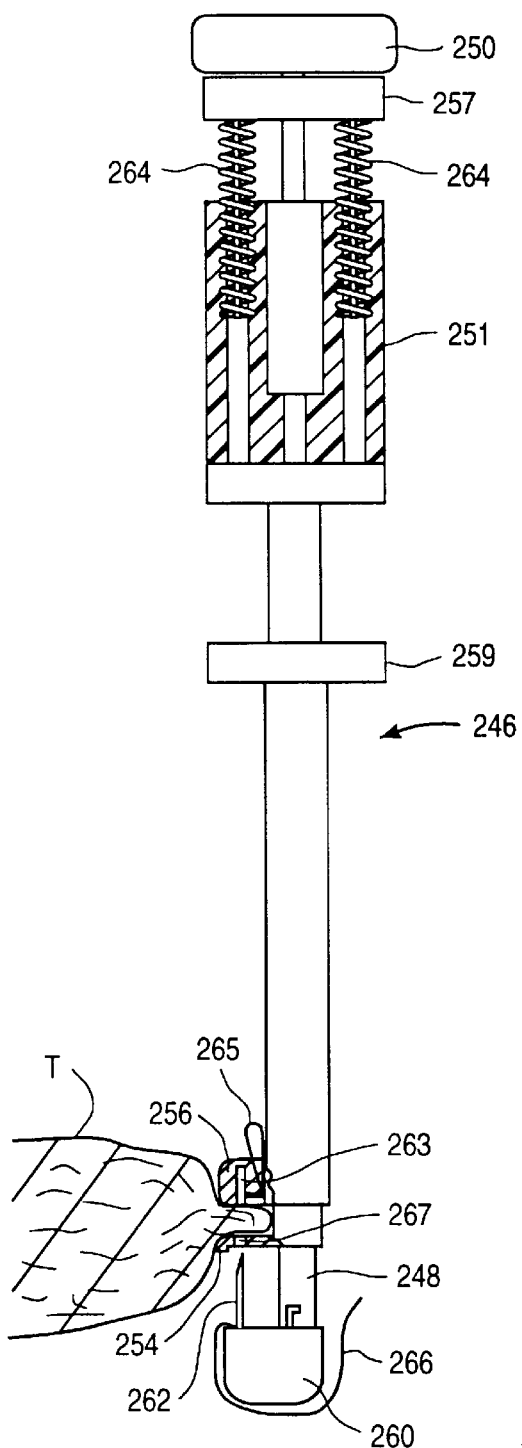

Referring to FIGS. 34 and 35, an exemplary embodiment of a suture placement device 246 having the ability to clamp the tissue T before placement of a suture will be described. The suture placement device 246 includes an elongate shaft 248 with a first sleeve 250 slidably mounted over the shaft 248, and a second sleeve 252 slidably mounted over the first sleeve 250. Shaft 248 is attached at its proximal end to a handle 258 slidable within a housing 251. One or more needles 262 are removably held in a needle carriage 260 fixed to the distal end of shaft 248. At the distal end of the first sleeve 250 is a first clamping member 254, and attached to the distal end of the second sleeve 252 is a second clamping member 256 (which also serves as a needle catch similar to the embodiments previously described). First sleeve 250 is attached at its proximal end to a first actuator 257 slidably mounted to housing 251 and biased proximally by springs 264. Second sleeve 252 is attached at its proximal end to a second actuator 259 slidable relative to first actuator 257.

Operation of the suture device 246 begins by positioning first clamping member 254 on the distal side of the tissue T, and distally translating second actuator 259 to slide the second sleeve 252 relative to the first sleeve 250 so as to clamp a section of the tissue T between first clamping member 254 and second clamping member 256, as illustrated in FIG. 35. Handle 258 is then pulled proximally relative to first and second actuators 257, 259 to drive needle 262 through tissue T. Handle 258 is pulled proximally until the needles 262 pass through an opening 267 in first clamping member 254 and are received within slot 263 in second clamping member 256. Needles 263 are retained in slot 263 by a leaf spring 265. The second actuator 259 is then proximally translated to the position illustrated in FIG. 34 to pull the needles 262 completely through the tissue T and to draw a suture 266 through the tissue T. The suture device 246 may then be withdrawn from the patient and the suture 266 tied as previously described.

Figure 36:
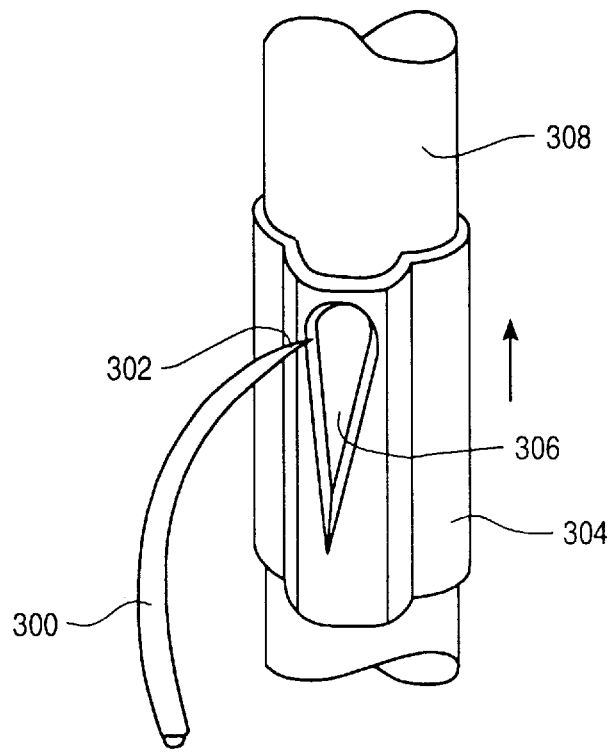
FIG. 36 illustrates an alternative embodiment of needle and needle catch having a tapered slot according to the present invention.
Figure 37:
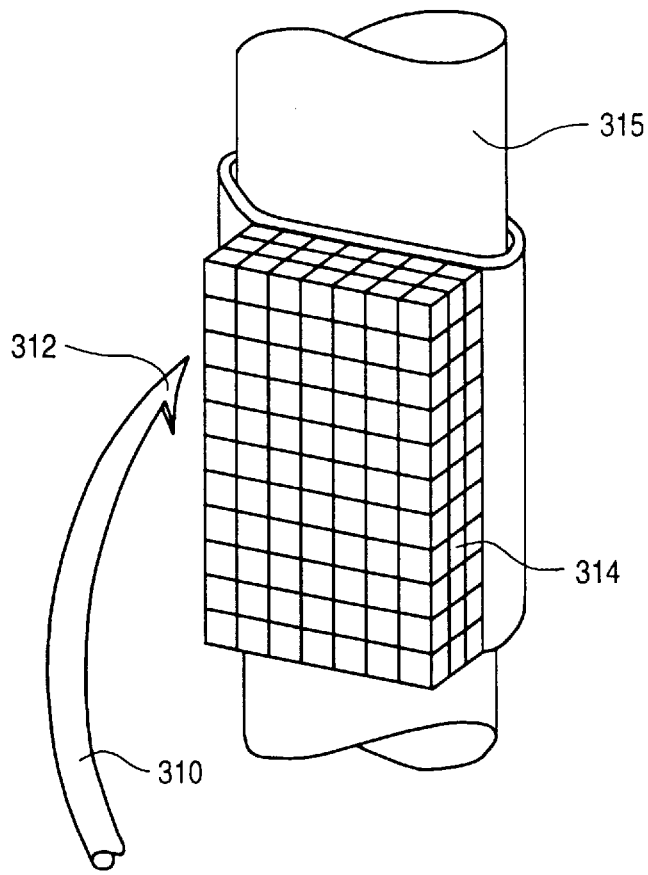
FIG. 37 illustrates an alternative embodiment of needle having a barb and needle catch constructed of a mesh material according to the present invention.

FIGS. 36 and 37 illustrate alternative embodiments of needles and corresponding needle catches that may be used with the suturing devices previously described herein. In FIG. 36, a needle 300 is provided along with a needle catch 304 which includes a tapered slot 306. The needle catch 304 will preferably be slidably mounted to a shaft 308 (which may be the shaft of any of the suturing devices described herein). When the needle 300 is passed through tissue, the needle 300 enters tapered slot 306 as shown. Catch 304 may then be translated upward to wedge needle 300 into the taper of slot 306 so as to prevent the needle 300 from being withdrawn from the catch 304. Preferably, catch 304 is constructed of an elastomeric material at least on either side of slot 306 to allow it to deform as needle 300 is forced into the slot.

In FIG. 37, a needle 310 is shown with a barb 312. A needle catch 314 is constructed of a porous mesh material, elastomer, gauze, or the like. Catch 314 may be placed on the shaft 315 of a suture device so that as the barb 312 is passed through tissue and toward the shaft, it will enter the catch 314. The barb 312 will snag the mesh material, thereby preventing removal of the needle 310 from the catch 314. Catch 314 may be fixed to the shaft of the suturing device, or slidable relative thereto so as to permit the needle to be drawn toward the proximal end of the device.

Figure 38:
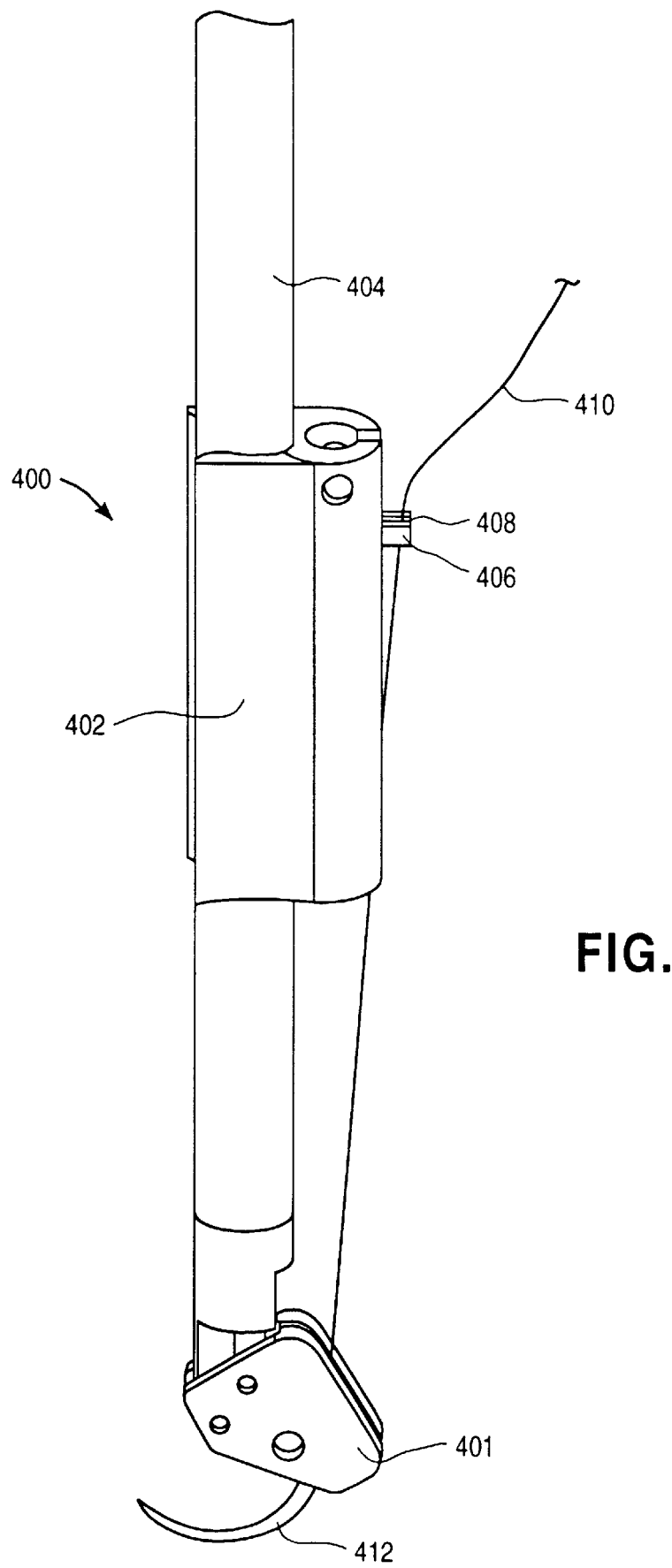
FIG. 38 is a perspective view of an alternative embodiment of a suturing device having a suture tensioning assembly.
Figure 39:
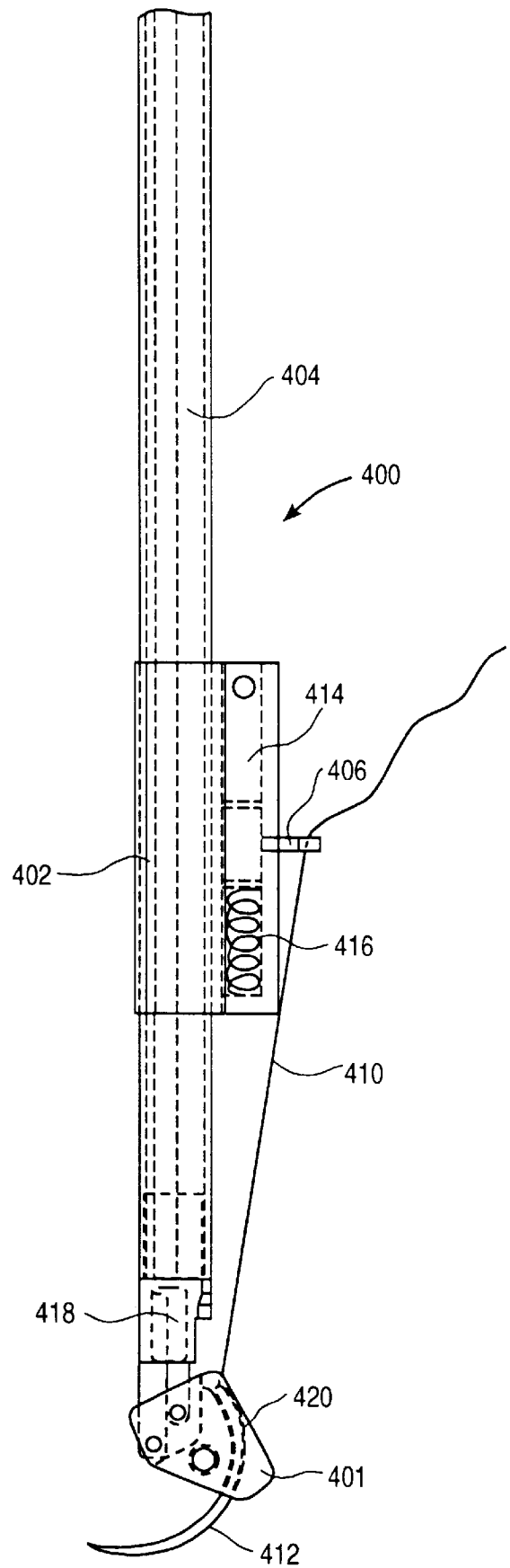
FIG. 39 is a side view of the suturing device of FIG. 38.

FIGS. 38 and 39 illustrate an alternative embodiment of a suture placement device 400 having a needle carriage 401 and a suture tensioning assembly 402. For convenience of discussion, device 400 is shown to be essentially identical to device 10 of FIG. 1 except for the construction of carriage 401. Although described in the context of suture device 400, assembly 402 may be used in connection with any of the embodiments previously described. Assembly 402 is employed to maintain a length of suture in tension while a needle is inserted into or withdrawn from tissue so that a surgeon will not be required to use a separate hand to grasp the suture. Assembly 402 may be integrally formed as part of a shaft 404 or may be slidably mounted to shaft 404. Assembly 402 includes an arm 406 having a slit 408 which securely holds a length of suture 410 (which in turn is connected to a needle 412).

As best shown in FIG. 39, arm 406 is axially slidable within a channel 414. A spring 416 or other compression member proximally biases arm 406 in channel 414 to keep suture 410 in tension. When a rod 418 is distally translated, carriage 401 pivots to drive needle 412 through tissue as previously described in connection with the embodiment of FIG. 1. As carriage 401 pivots, arm 406 is drawn distally, increasing the tension in suture 410, causing spring 416 to compress. In this way, tension is maintained in suture 410 as carriage 410 is pivoted. In the event that carriage 401 is pivoted in the reverse direction (such as when needing to withdraw the needle from tissue and retry placement), spring 416 expands to maintain tension in suture 410. Advantageously, assembly 402 may optionally serve to securely hold needle 412 in carriage 401 by maintaining sufficient tension on suture 410 to pull needle 412 into a slot 420.

While the above is a complete description of the preferred embodiments of the invention, various alternatives, modifications and equivalents may be used. Therefore, the above description should not be taken as limiting the scope of the invention, which is defined by the appended claims.

What is claimed is:

1. A suturing device, comprising:
    an elongate shaft having a distal end and a proximal end;
    a needle carriage movably attached to the distal end of the shaft, the needle carriage having a removable portion, a non-removable portion, and a coupling mechanism for releasably connecting the removable portion of the needle carriage to the non-removable portion;
    at least one needle removably secured to the removable portion of needle carriage; and
    means for driving the needle carriage so as to move the needle relative to the shaft.

2. The suturing device as in claim 1, wherein the needle carriage is pivotally connected to the shaft so that the needle may be rotated within a plane at an angle of 0°±45° relative to the axis of the shaft.

3. The suturing device as in claim 1, wherein the carriage is attached so as to pivot through an angle of at least about 90° relative to a longitudinal axis of the shaft.

4. The suturing device as in claim 1, further comprising a rod slidably coupled to the shaft and connected to the carriage to pivot the carriage relative to the shaft by the sliding motion of the rod.

5. The suturing device as in claim 1, further comprising an actuator at the proximal end of the shaft and a linkage coupled between the actuator and the driving means.

6. The suturing device as in claim 4, wherein the actuator further comprises a means for locking the actuator in a position.

7. The suturing device as in claim 6, wherein the locking means locks automatically when the needle has been driven through said arc.

8. The suturing device as in claim 1, wherein the shaft has a length of at least 20 cm.

9. The suturing device as in claim 1, wherein the shaft, needle carriage, needle, and means for driving the needle carriage are configured to pass through a tubular space of at most about 30 mm in diameter.

10. The suturing device as in claim 1, wherein the needle is curved.

11. The suturing device as in claim 10, wherein the needle has a center of curvature, and the carriage is pivotable about a pivot point, the needle being secured to the carriage such that the center of curvature is disposed at the pivot point.

12. The suturing device as in claim 1, wherein the carriage further comprises a releasing mechanism for releasing the removable portion from the non-removable portion.

13. The suturing device as in claim 12, wherein the releasing mechanism comprises a snap fitting on the removable portion of the carriage.

14. The suturing device as in claim 1, wherein the carriage is constructed of a plastic that is disposable.

15. The suturing device of claim 1, wherein the needle carriage includes a slot sized to slidably receive a proximal end of the needle until the proximal end of the needle, and means for securing the needle in the 'slot.

16. The suturing device of claim 15, wherein the slot is sized to fictionally engage the needle, whereby the needle may be withdrawn from the slot by pulling the needle to overcome the friction within the slot.

17. The suturing device as in claim 16, wherein a sharpened distal tip of the needle remains outside the carriage when the needle is disposed in the slot.

18. The suturing device as in claim 15, wherein the needle has a length and at least about one-half of the length remains outside the carriage when the needle is disposed in the slot.

19. A method for placing a suture in the annulus of a heart valve by accessing the valve through a port in a patient's chest, the method comprising:

positioning a needle attached to a suture in the patient's heart, the needle being carried by a needle holder removably attached to an elongated shaft extending through the port;

directing the needle into the annulus while visualizing through the port placement of the needle into the annulus;

passing the needle through the annulus by manipulating an actuator at a proximal end of the shaft from outside the patient's chest; and removing the needle holder from the shaft.

20. The method as in claim 19, further comprising the step of attaching a different needle holder to the shaft after the step of removing.

21. The method as in claim 19, wherein the needle has a radius of curvature and the step of passing the needle through the annulus comprises passing the needle along an arc having a radius substantially conforming to the radius of curvature of the needle.

22. A method for placing a suture in tissue adjacent an opening in a body structure, the method comprising:

providing at least one needle having a sharpened tip and a passage extending longitudinally therethrough, the needle being attached to a suture and coupled to a distal end of an elongated shaft;

directing the sharpened tip of the needle into the tissue adjacent the opening in the body structure;

passing the needle through the tissue by manipulating an actuator located at a proximal end of the shaft;

threading the suture through the passage in the needle after the needle has been passed through the tissue; and applying a vacuum to the passage in the needle to assist in threading the suture through the passage.

23. The method as in claim 22, wherein the needle has a radius of curvature and the step of passing the needle through the tissue is carried out by moving the needle along an arc having a radius substantially conforming to the radius of curvature of the needle.

* * * * *